United States Patent [19]

Bowman et al.

[11] Patent Number: 5,755,894
[45] Date of Patent: May 26, 1998

[54] ENDOSCOPIC CANNULATED INSTRUMENT FLUSHING APPARATUS FOR FORCING A CLEANING SOLUTION THROUGH AN ENDOSCOPIC CANNULATED INSTRUMENT FOR REMOVAL OF GROSS DEBRIS

[75] Inventors: Michael D. Bowman, Olathe; Michael J. Armentrout, Leawood, both of Kans.; Drake L. Koch, Kansas City, Mo.

[73] Assignee: Minnesota Mining and Manufacturing Company, St. Paul, Minn.

[21] Appl. No.: 465,248

[22] Filed: Jun. 5, 1995

Related U.S. Application Data

[63] Continuation of Ser. No. 130,597, Oct. 1, 1993, Pat. No. 5,511,568, which is a continuation-in-part of Ser. No. 47,119, Apr. 14, 1993, Pat. No. 5,279,317, which is a continuation-in-part of Ser. No. 22,994, Feb. 26, 1993, abandoned.

[51] Int. Cl.$^6$ ............................................. B08B 9/02
[52] U.S. Cl. ................... 134/22.12; 134/24; 134/169 C; 134/166 C
[58] Field of Search ............................. 134/169 C, 166 C, 134/94.1, 95.1, 22.11, 22.12, 24; 137/625.13, 625.15, 625.16, 625.19, 625.4, 625.41

[56] References Cited

U.S. PATENT DOCUMENTS

| | | | |
|---|---|---|---|
| 558,553 | 4/1896 | Forslund et al. | 137/625.19 |
| 1,589,721 | 6/1926 | Schwaner. | |
| 1,903,915 | 4/1933 | Smith | 134/169 C |

(List continued on next page.)

FOREIGN PATENT DOCUMENTS

| | | |
|---|---|---|
| 145219 | 11/1935 | Austria . |
| 0 038 168 | 10/1981 | European Pat. Off. . |
| 0 072 257 | 2/1983 | European Pat. Off. . |
| 0 452 790 | 6/1994 | European Pat. Off. . |
| 32224 | 9/1927 | France . |
| 79 20613 | 2/1981 | France . |

(List continued on next page.)

OTHER PUBLICATIONS

PCT International Preliminary Examination Report PCT/US94/00501, dated Apr. 16, 1995. (4 pages).
PCT Written Opinion PCT/US94/00501. (3 pages).
"Introducing The AC-5002M" 6 page brochure, Chris Lutz Medical.

(List continued on next page.)

*Primary Examiner*—Frankie L. Stinson
*Attorney, Agent, or Firm*—Jeffrey J. Hohenshell; Walter N. Kirn; Gary L. Griswold

[57] ABSTRACT

An endoscopic instrument cleaning apparatus includes a syringe coupled to a flushing chamber by a form-fitting stopper. A distal, or instrument receiving end of the flushing chamber is inserted into a supply of cleaning fluid and the plunger of the syringe is drawn out to its fully retracted length, thereby filling the syringe and the flushing chamber with cleaning fluid. Then the distal end of an endoscopic instrument is inserted about through an aperture in a stopper having the shape of a conical frustum and is inserted into the flushing chamber to a depth of about 4 inches (10 cm) and the plunger of the syringe is thrust forward to inject pressurized cleaning solution through the endoscopic instrument. In another embodiment, the syringe receiving stopper is recessed within a proximal end of the flush chamber by about ⅜ inches (0.95–1.00 cm) and a tightly fitting tubular insert is glued into the recess to eliminate the possibility that the syringe receiving stopper will be blown out of the flushing chamber by fluid pressure when it is used. Alternatively, an inward projecting lip is formed in the distal end of the flush chamber for the same purpose. A rectangular flushing board includes a neck having a pair of aligned yokes for seating and holding the syringe body to eliminate wrist and thumb strain. In another embodiment, a flushing chamber is formed as an extension to the body of a syringe, thereby eliminating the need for a separate flushing chamber.

2 Claims, 12 Drawing Sheets

U.S. PATENT DOCUMENTS

| | | | |
|---|---|---|---|
| 1,991,608 | 2/1935 | Frazier . | |
| 2,211,892 | 8/1940 | Giese | 141/1 |
| 3,039,477 | 6/1962 | Harbo | 134/169 C |
| 3,039,492 | 6/1962 | Brucker | 137/625.41 |
| 3,434,882 | 3/1969 | Carolin | 134/95.1 |
| 3,577,279 | 5/1971 | Lightner et al. | 134/95.1 |
| 3,686,502 | 8/1972 | Sieber | 250/52 |
| 3,690,333 | 9/1972 | Kerner | 134/95.1 |
| 3,721,252 | 3/1973 | Ayella | 134/122 |
| 3,963,438 | 6/1976 | Banez | 21/58 |
| 4,059,123 | 11/1977 | Bartos et al. | 134/102 |
| 4,064,886 | 12/1977 | Heckele | 134/95 |
| 4,238,054 | 12/1980 | Chen | 222/131 |
| 4,281,646 | 8/1981 | Kinoshita | 128/6 |
| 4,288,882 | 9/1981 | Takeuchi | 15/88 |
| 4,525,220 | 6/1985 | Sasa et al. | 134/21 |
| 4,667,691 | 5/1987 | Sasa | 134/169 C |
| 4,748,007 | 5/1988 | Gaudion et al. | 422/300 |
| 4,763,678 | 8/1988 | Ott | 134/171 |
| 4,941,593 | 7/1990 | Hicks et al. | 222/148 |
| 4,967,960 | 11/1990 | Futrell | 239/148 |
| 4,991,608 | 2/1991 | Schweiger | 134/56 |
| 5,064,123 | 11/1991 | Aiello et al. | 239/706 |
| 5,076,472 | 12/1991 | Gross et al. | 222/144.5 |
| 5,090,433 | 2/1992 | Kamaga | 134/169 |
| 5,133,374 | 7/1992 | Druding et al. | 134/104.2 |
| 5,225,001 | 7/1993 | Mann et al. | 134/169 C |
| 5,245,845 | 9/1993 | Langford | 68/3.055 |
| 5,279,317 | 1/1994 | Bowman et al. | 134/166 |
| 5,279,799 | 1/1994 | Moser | 422/292 |
| 5,320,119 | 6/1994 | Griffiths | 134/95.1 |
| 5,425,815 | 6/1995 | Parker et al. | 134/26 |
| 5,443,801 | 8/1995 | Langford | 422/294 |
| 5,494,637 | 2/1996 | Barlow | 422/28 |
| 5,511,568 | 4/1996 | Bowman et al. | 134/102.2 |
| 5,518,501 | 5/1996 | Oneda et al. | 600/127 |

FOREIGN PATENT DOCUMENTS

| | | |
|---|---|---|
| 650 330 | 8/1935 | Germany . |
| 25 40 263 | 3/1977 | Germany . |
| 294 47 576 | 6/1980 | Germany . |
| 29 08 612 | 9/1980 | Germany . |
| 29 31 366 | 2/1981 | Germany . |
| 34 05 268 | 9/1985 | Germany . |
| 3413386 | 10/1985 | Germany . |
| 3443912 | 6/1986 | Germany . |
| 3835861 | 4/1995 | Germany . |
| 7-116117 | 5/1995 | Japan . |
| WO 79/00620 | 9/1979 | WIPO . |
| WO/94/19117 | 9/1994 | WIPO . |

OTHER PUBLICATIONS

Journal of healthcare materiel management, various pages, Aug. 1994.

"The Reliable High Speed Replacement for Flash Sterilization" 1 page brochure, Joslyn Sterilizer Corporation.

"From Getinge for Hospitals Across the World" 18 page German brochure with English translation, Getinge.

"Why Medisafe Beats Other Ultrasonic Cleaners Inside and Out", 1 page brochure, Sharn Inc.

"Washer Disinfector 4656", 6 page brochure, Getinge Disinfection, Inc.

"Reinigungs, Desinfektions und Trocknungsautomat GE–DE 4656", 6 pagae German brochure, Getinge, 1995.

"Sterile Processing . . . Just in Time" r page brochure, Steris Corporation. ©1995 Note patents cited on last page.

"Sterile System 1™ Sterile Processing System" 2 page brochure, Steris Corporation.

Lancer Product Brochure, 40 page brochure.

"HAMO T–21 Cleaning, decontaminating and drying unit for hospitals, laboratories, pharmacies, research and industry" 6 page brochure, HAMO Med. Corp., Oct. 1995.

"Endocleaner™ Instrument Processing System", 1 page brochure, Aesculap.

"The Endo–Clean™ System Takes the Problems Out of Cleaning Endoscopic Instruments" 1 page brochure, Snowden–Pencer, 1994.

"New Products to Assist Endoscopic Cleaning and Sterilization" 1 page brochure, Davis+Geck Endosurgery, 1994.

"To the Power of Ten" 1 page brochure, Custom Ultrasonics Incorporated.

"Is Sterile Clean?" 1 page brochure, Custom Ultrasonics Incorporated.

"Cleaning and Disinfection of MIC and Micro–Instruments", 9 page German brochure with Informal English translation, Miele Professional.

"Competent Partner for Validated Cleaning" 8 page German article with Informal English translation, the Journal Krankenhaus Technik, Nov. 1995.

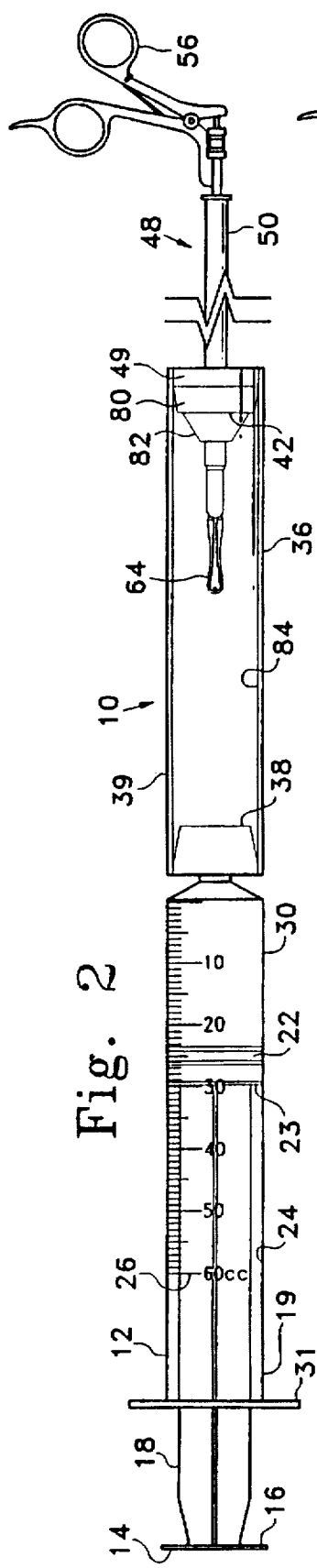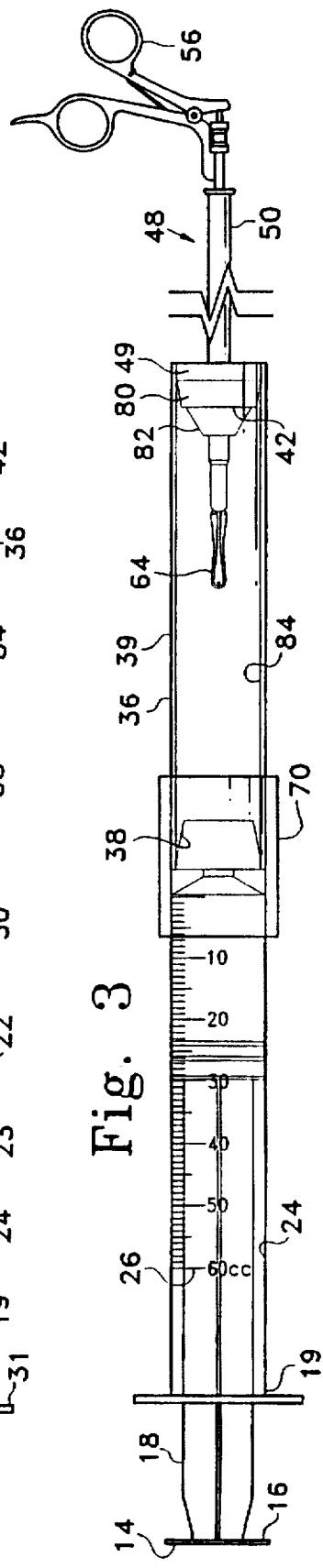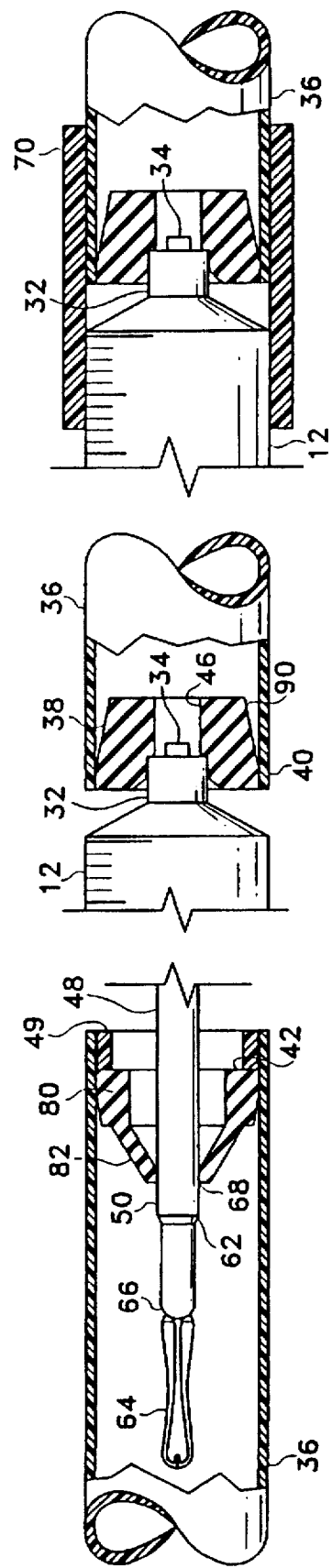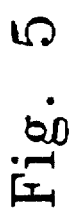

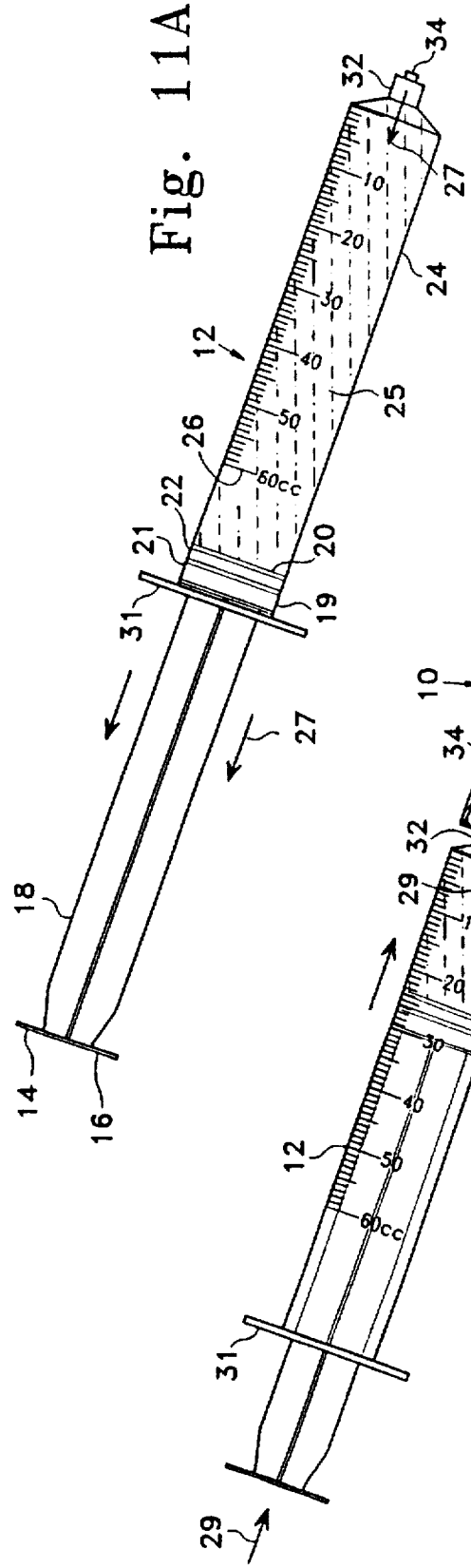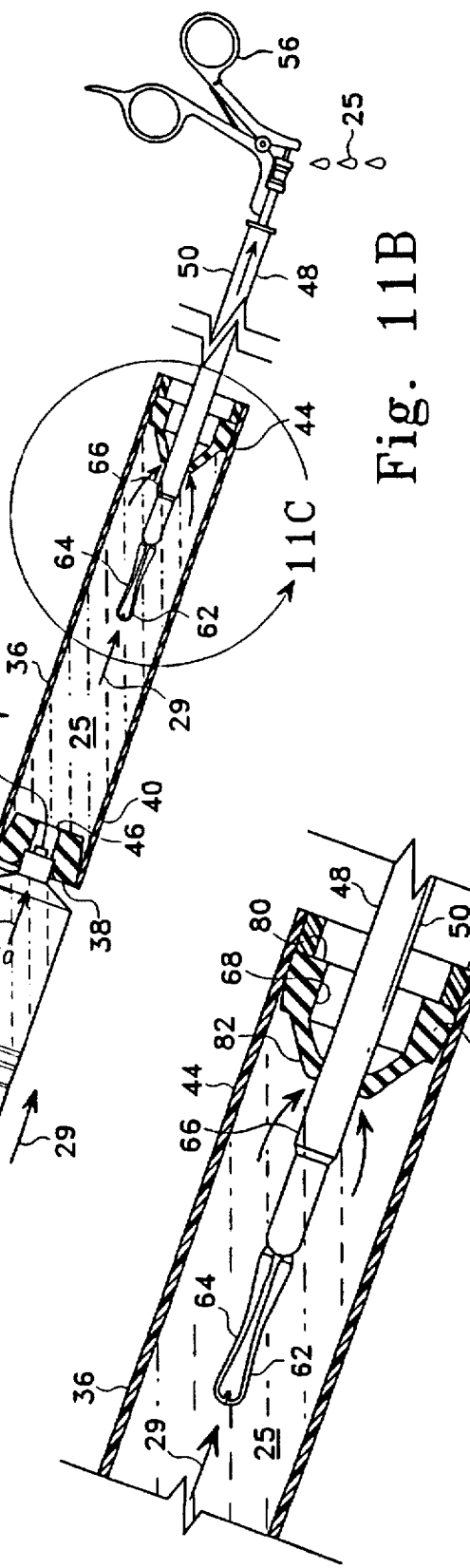

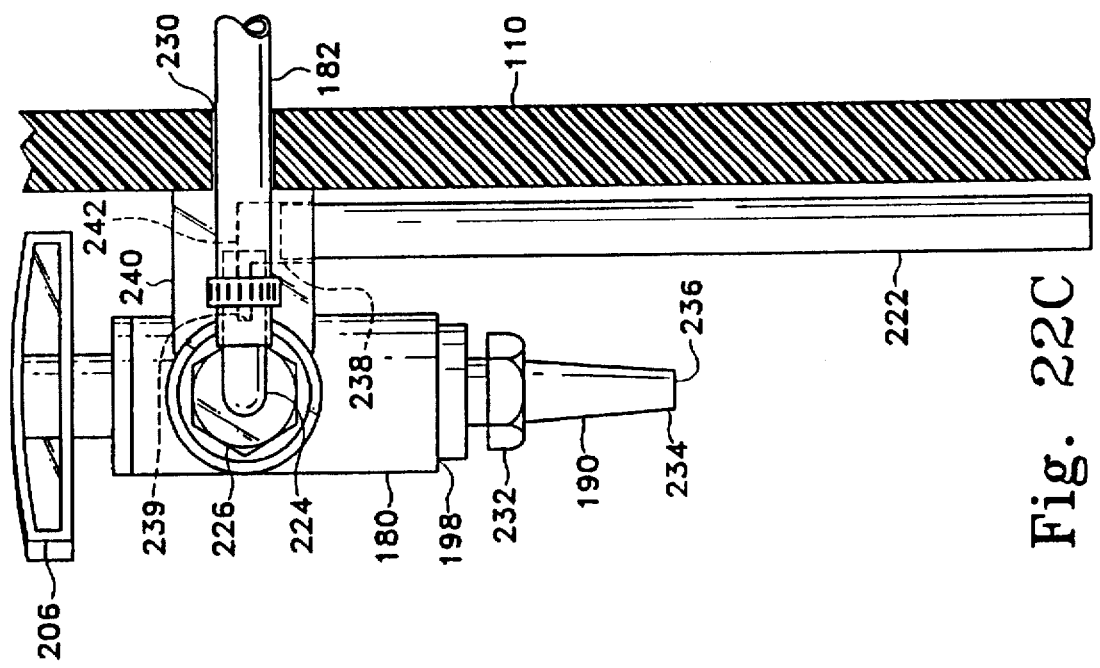
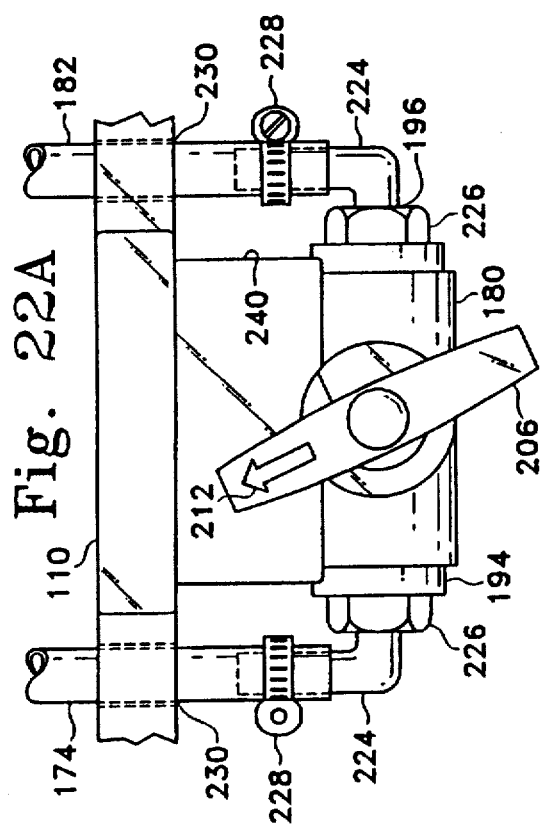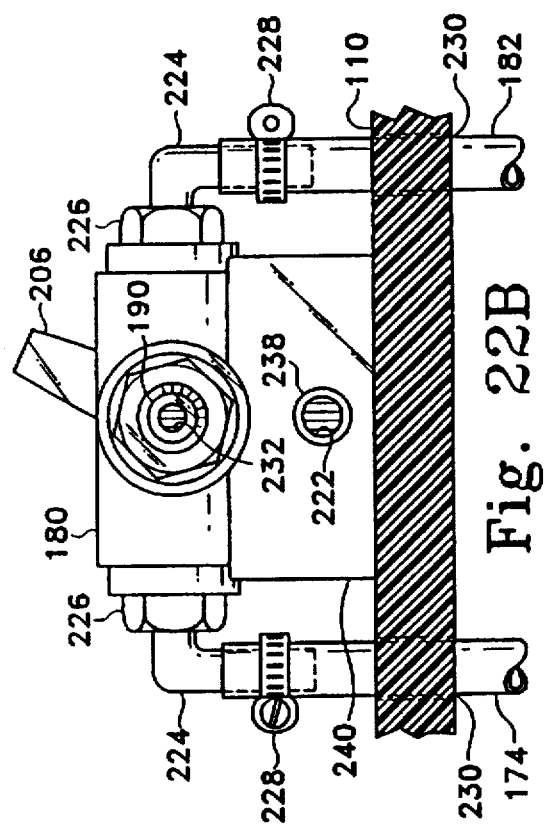

ENDOSCOPIC CANNULATED INSTRUMENT FLUSHING APPARATUS FOR FORCING A CLEANING SOLUTION THROUGH AN ENDOSCOPIC CANNULATED INSTRUMENT FOR REMOVAL OF GROSS DEBRIS

CROSS-REFERENCE TO RELATED APPLICATIONS

This Application is a continuation of U.S. patent application Ser. No. 08/130,597 filed Oct. 19, 1993 now U.S. Pat. No. 5,511,568 which was a Continuation-In-Part of U.S. patent application Ser. No. 08/47,119, filed Apr. 14, 1993, now U.S. Pat. No. 5,279,317, which is a Continuation-In-Part of U.S. patent application Ser. No. 08/22,994, filed Feb. 26, 1993, now abandoned.

BACKGROUND OF THE INVENTION

1. Field of the Invention

The present invention is related to an apparatus and process for cleaning endoscopic surgical instruments by flushing the cannula. More particularly, the present invention is directed to a hand-operated apparatus for forcing a cleaning solution through an endoscopic cannulated surgical instrument to remove gross debris from surgery that utilizes a syringe or other source of pressurized cleaning solution to provide the motive power required for forcing a cleaning solution through the cannula of an endoscopic cannulated instrument. In a preferred embodiment, the present invention includes pressurized tanks for delivering a steady flow of flushing solutions through an endoscopic cannulated instrument.

2. Description of Related Art Including Information Disclosed Under 37 C.F.R. Sections 1.97–1.99

Increasingly, surgeries are conducted with endoscopic cannulated instruments, or instruments, which are inserted through minimal surgical openings in the body to reduce the invasiveness of surgical procedures. Endoscopic instruments are long instruments having a narrow elongated sleeve or housing with cables, rods and the like being threaded through them and connected to tools on the working, or distal, end that are manipulated by squeezing scissors-like handles, or other control mechanism, on the other, proximal end, which remains outside the patient. Many endoscopic instruments have a rigid outer housing and a rod reciprocates inside the housing to actuate a surgical tool on the distal end of the endoscopic instrument. Other endoscopic instruments are flexible and are used primarily in conjunction with a cannulated endoscope. For purposes of this disclosure, an endoscopic instrument includes all instruments used in minimally invasive surgery and having an elongated housing or sleeve that forms a cannula that houses any type of control mechanism, e.g., rod or cable, to control a tool or instrument for use inside a patient's body. The present invention is directed to an apparatus for cleaning gross debris from any such type of medical instrument by flushing the cannula.

All these instruments are cannulated instruments, that is, each has an elongated cannula, which is almost completely filled with instrument and controls. It is the cannula that traps gross debris, which is invariably drawn into the cannula when the control rods, wires, and the like reciprocate within the cannula formed by the outer housing or sleeve of endoscopic instruments.

During use, endoscopic instruments draw bodily fluids and tissues and other matter from the patient, known collectively as "gross debris," into the elongated tubular housing of the endoscopic instrument. These tubes are quite small and most of their volume is filled with the control rod or the like, leaving little room for cleaning. The sleeve or housing of endoscopic instruments are not sealed, and the reciprocal movement of the inner workings within the sleeve invariably draws gross debris into the sleeve, from which it cannot be removed effectively using devices currently known in the medical profession. Further, surgeons operating inside the abdominal cavity pressurize the abdominal cavity with carbon dioxide to separate organs and tissues from one another and this pressurized gas leaks through cannulated instruments, forcing gross debris into the housing of the endoscopic or cannulated instruments.

Because there is virtually no way to disassemble reusable instruments, they tend to trap blood, other fluids, and tissue in the space between the tool control rod and the housing. This gross matter inhibits the ability of pressurized steam, ethylene oxide or chemical sterilants to effectively reach all parts of the instrument. Further, the space between the housing and the instrument control rod typically harbors spores, which are not killed by enzymatic cleaners, but can only be killed by steam or appropriate gas, such as ethylene oxide. Gross debris, however, frequently covers spores or surrounds them, reducing the efficacy of either steam or ethylene oxide to reach and kill them. This may allow spores or other blood-borne pathogens to survive inside the housing, greatly increasing the risk of patient infection from cross contamination from other patients. Even if it were possible to disassemble cannulated instruments for thorough cleaning, it would be prohibitively expensive and time consuming to do so.

Endoscopic instruments are cleaned and sterilized according to hospital protocol, which varies widely between institutions. In some cases, endoscopic instruments are sterilized during the night, in a process that takes about at least 30 minutes. During the day, however, they may be repeatedly used for consecutive surgeries on different patients with minimally accepted cleaning and sterilization practices, partly because hospital staff cannot afford to take the time required for complete sterilization. With the increase of endoscopic procedures and lack of proper cleaning techniques, gross debris build up is probable and potentially widespread. In the age of AIDS, and contagious hepatitis type B, this situation is obviously of great concern, which has been recognized, but not solved, by the medical community.

Currently about 2.2 million surgical procedures employing endoscopic instrument are performed each year. It is estimated that by the year 2000 more than one-half of all surgeries will performed with minimally invasive techniques, that is, with endoscopic instrument, which will be about 11 million surgeries per year. The potential for serious cross-contamination between patients and resulting transmission of disease is clear, but no clear, effective and affordable solution to the problem is known.

Some approaches to addressing the problem of removing gross debris from the exterior of endoscopes, which are tightly sealed and do not admit debris, as they have no cannula, have led to issued patents, some of which are discussed below. No issued patents specifically directed to removing gross debris from the cannula of endoscopic cannulated instruments, however, have been located.

U.S. Pat. No. 4,667,691, issued to Sasa on May 26, 1987 (Sasa '691), discloses a "Device for Cleaning channels of an Endoscope" comprising syringe provides the power to force a liquid cleaning solution through an endoscope through a complex series of valves and tubing. The fluid flows first through a main body, into which it is drawn from a fluid storage tank and from which it is forced into the tubing, other valves, and the endoscope and so forth.

U.S. Pat. No. 4,525,220, issued to Sasa et al. on Jun. 25, 1985 (Sasa et al. '22), discloses a "Method of Cleaning Endoscope Channels" comprising a number of methods of using the device disclosed and claimed in Sasa '691, which is described above.

U.S. Pat. No. 4,439,884, issued to Giorni on Apr. 3, 1984 (Giorni '884) discloses a "Container with Bristles for Cleaning Instruments" comprising a cylindrical vessel with an open top. A plurality of bristles project horizontally and inwardly from the inside side wall toward the center of the vessel. The vessel is filled with an appropriate cleaning fluid. The instrument is submerged in the fluid and is rotated by hand to clean it. If desired, the instrument may be supported by a ring 9 connected to a clamp 10 on the outside of the vessel.

U.S. Pat. No. 4,288,882, issued to Takeuchi on Sep. 15, 1981 (Takeuchi '882), discloses an "Endoscope Sheath Cleaning Device" comprising a bulky free-standing machine having a J-shaped tube into which an endoscope sheath is inserted progressively and repeatedly, either by hand or machine, while water or other solution is sprayed on it from two opposed nozzles located near the top of the apparatus. The spray from the nozzles is directed downward onto a brush set which brushes the exterior of the sides of the endoscope. It does not appear that any fluid is forced through the endoscope by this apparatus.

U.S. Pat. No. 4,281,646, issued to Kinoshita on Aug. 4, 1981 (Kinoshita 646), comprises a window washer for cleaning the observation window at the end of an endoscope having an observation window, while the endoscope is in use.

None of these devices is directed to removing gross debris from the cannula of endoscopic cannulated surgical instruments in general. Moreover, none of these devices offers an inexpensive, disposable and reliable endoscopic cannulated instrument cleaning apparatus for removing gross debris from the cannula that is also simple, convenient and easy to use and to manufacture. Further, none of these devices offers a comprehensive system for cleaning a large number of instruments without stopping for additional flushing solutions. Therefore, a serious need exists for an endoscopic cannulated instrument cleaning apparatus that is inexpensive, disposable and reliable, while also being simple, convenient and easy to use and to manufacture and that allows for cleaning a large number of instruments without stopping for additional flushing solutions. Such an apparatus is disclosed and claimed in this document, as follows.

SUMMARY OF THE INVENTION

Accordingly, it is a primary object of the present invention to provide an endoscopic cannulated instrument cleaning apparatus capable of flushing gross debris from an endoscopic cannulated instrument.

It is another object of the present invention to provide an endoscopic cannulated instrument cleaning apparatus that is simple, convenient and easy to use.

It is another object of the present invention to provide an endoscopic cannulated instrument cleaning apparatus that is inexpensive, simple, convenient and easy to manufacture.

It is another object of the present invention to provide an endoscopic cannulated instrument cleaning apparatus that is disposable.

It is another object of the present invention to provide an endoscopic cannulated instrument cleaning apparatus that provides a complete system capable of providing sufficient pressurized flushing solutions to clean a large number of endoscopic cannulated surgical instruments without recharging, while retaining the characteristics of being easy and inexpensive to manufacture.

An endoscopic cannulated instrument cleaning apparatus according to the present invention is a flushing device designed to help clear cannulated instruments of gross material as part of the cleaning process. Preferably, it is for single patient use and is disposable. The endoscopic cannulated instrument cleaning apparatus is manufactured in sizes that fit most cannulated instruments. Regular use of the endoscopic cannulated instrument cleaning apparatus helps extend the life of expensive cannulated surgical instruments and reduces the risk of patient infection from cross contamination.

In use, it is important to follow all hospital and other indicated protocol for cleaning and processing instruments. In a preferred embodiment, a 60 cc syringe is connected to a flushing chamber. Then the distal end of the endoscopic instruments cleaning apparatus is submerged into a flushing solution and the syringe plunger is retracted to fill the flush chamber with flushing solution. Next, the worker opens or disassembles all necessary exit ports on a cannulated instrument having flush ports to allow a free flow of the flushing solution. Then the distal end of the endoscopic or cannulated surgical instrument is inserted into the flush chamber a sufficient distance to insure that the distal end of the housing is within the flush chamber. To flush gross material from the endoscopic or cannulated instrument, depress the syringe plunger until a desired amount of flushing solution enters and exits the instrument. The present invention is an aid to the over-all cleaning process and is not intended to replace other elements of hospital protocol. Currently used hospital protocols, however, do not remove gross debris from the cannula of these instruments. Consequently, although the instruments may be thoroughly sterilized, organic matter trapped inside the cannula provides a prime culture medium for bacteria growth. And, of course, if the instrument is not thoroughly sterilized, bacteria or viruses may survive inside the cannula, where it may have a good culture medium. Such debris, bacteria, and virus may be introduced into another patient during a later-performed surgery.

In the preferred embodiment described herein, a syringe is used to provide the force necessary for flushing the cannula of an endoscopic cannulated instrument with a cleaning or flushing solution. This source of pressurized cleaning solution has been selected because it is inexpensive, disposal, and readily available at any hospital. Other sources of pressurized flowing cleaning, or flushing, solution could easily be used, including, for example, hand or foot operated pumps, electrical pumps, and the like. These are more expensive and more difficult to obtain, especially in the instrument cleaning and sterilizing departments of hospitals, which typically have only small budgets.

When a syringe is used to provide a source of pressurized flushing solution, it has been found that some workers experience soreness in the wrist and thumb when using the present invention to flush several or many endoscopic cannulated surgical instruments. This minor difficultly has been overcome by providing a flushing board having a pair of yokes fixed to a neck of the flushing board by stainless steel screws, with each yoke including a U-shaped channel sized to readily hold the cylindrical body of a syringe. The handle portion of the syringe is placed on the outside or upper side of a proximal yoke. The handle is wider than the U-shaped channel in the yoke, so the yoke holds the syringe in place, allowing the worker to press against the syringe plunger with his palm while keeping her wrist straight. This has completely eliminated the need to use the thumb and has completely eliminated user fatigue and soreness.

In another preferred embodiment, which embodies the best mode now known to the inventors for practicing their invention, the present invention includes a pair of plastic sprayer tanks connected to a valve by flexible lines. The valve allows liquid to flow from one tank at a time into and through a valve seated on a flushing board. The valve directs the flow of liquid through a tapered nozzle that is connected to a flush chamber. One tank typically holds a supply of pressurized enzymatic cleaner, which is flushed through the endoscopic cannulated surgical instrument first for a few seconds. Then the valve is manually turned so that it shuts off the supply of liquid from the enzymatic cleaner tank and turns on the flow of liquid from the pressurized rinsing tank, which is also allowed to run for a short while. Then the valve is turned off. Any pressure in the valve is bled off by a pressure release opening. The pressurized tanks are like typical small garden sprayer tanks and are pressurized as needed to maintain an operating range of pressure of about 15–30 psi ($1.03$–$2.07 \times 10^6$ dynes/cm$^2$), with a pressure of about 20 psi ($1.37 \times 10^6$ dynes/cm$^2$) being preferred, by means of a self-contained hand compressor. Naturally, other means for delivering pressurized liquids to the apparatus could also be used, such as large automatically pressurized tanks with electrical compressors, and so forth.

Other objects and advantages of the present invention will become apparent from the following description taken in connection with the accompanying drawings, wherein is set forth by way of illustration and example, the preferred embodiment of the present invention and the best mode currently known to the inventors for carrying out their invention.

BRIEF DESCRIPTION OF THE DRAWINGS

FIG. 2 is a side elevation of the endoscopic cannulated instrument flushing apparatus of FIG. 1 shown with the plunger of the syringe in a position preparatory to the cleaning stroke.

FIG. 3 is a side elevation of the endoscopic cannulated instrument flushing apparatus of FIG. 1 shown with a bracing sleeve for reenforcing the connection between the syringe and the flush chamber.

FIG. 4 is an enlarged cross sectional elevation of the endoscopic instrument flushing apparatus of FIG. 1 showing the instrument cleaning end of the endoscopic instrument cleaning apparatus with an instrument in place.

FIG. 5 is an enlarged cross sectional elevation of the endoscopic cannulated instrument flushing apparatus of FIG. 1 showing the syringe accepting end of the endoscopic instrument flushing apparatus.

FIG. 6 is an enlarged cross sectional elevation of the endoscopic cannulated instrument flushing apparatus of FIG. 3 showing the syringe accepting end of the present invention, and the bracing sleeve about the ends of the syringe and the tubular flushing chamber, where the two respective parts mate.

FIG. 11A is a side elevation of a syringe that forms a portion of the endoscopic cannulated instrument cleaning apparatus according to the present invention, showing the plunger of the syringe drawn outward preparatory to it maximum stroke.

FIG. 11B is a side elevation, partially in cross section, of an endoscopic cannulated instrument flushing apparatus according to the present invention showing the syringe in about mid-stroke during cleaning of an instrument and illustrating the effect of the fluid flow on the instrument retaining stopper.

FIG. 11C is an enlarged fragmentary cross sectional view of the instrument receiving portion of the endoscopic cannulated instrument flushing apparatus of FIG. 11B, enlarged from the circled "FIG. 11C" portion of FIG. 11B.

FIG. 22A is a top plan view of the valve assembly taken along the lines 22A—22A of FIG. 19.

FIG. 22B is a bottom plan view of the valve assembly taken along the lines 22B—22B of FIG. 19.

FIG. 22C is a side elevation of the valve assembly taken along lines 22C—22C of FIG. 19.

DETAILED DESCRIPTION OF THE PREFERRED EMBODIMENTS

As required by the Patent Statutes and the case law, the preferred embodiment of the present invention and the best mode currently known to the inventors for carrying out the invention are disclosed in detail herein. The embodiments disclosed herein, however, are merely illustrative of the invention, which may be embodied in various forms. Therefore, specific structural and functional details disclosed herein are not to be interpreted as limiting, but merely to provide the proper basis for the claims and as a representative basis for teaching one skilled in the art to which the invention pertains to make and use the apparatus and process disclosed herein as embodied in any appropriately specific and detailed structure.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

Figure 1:
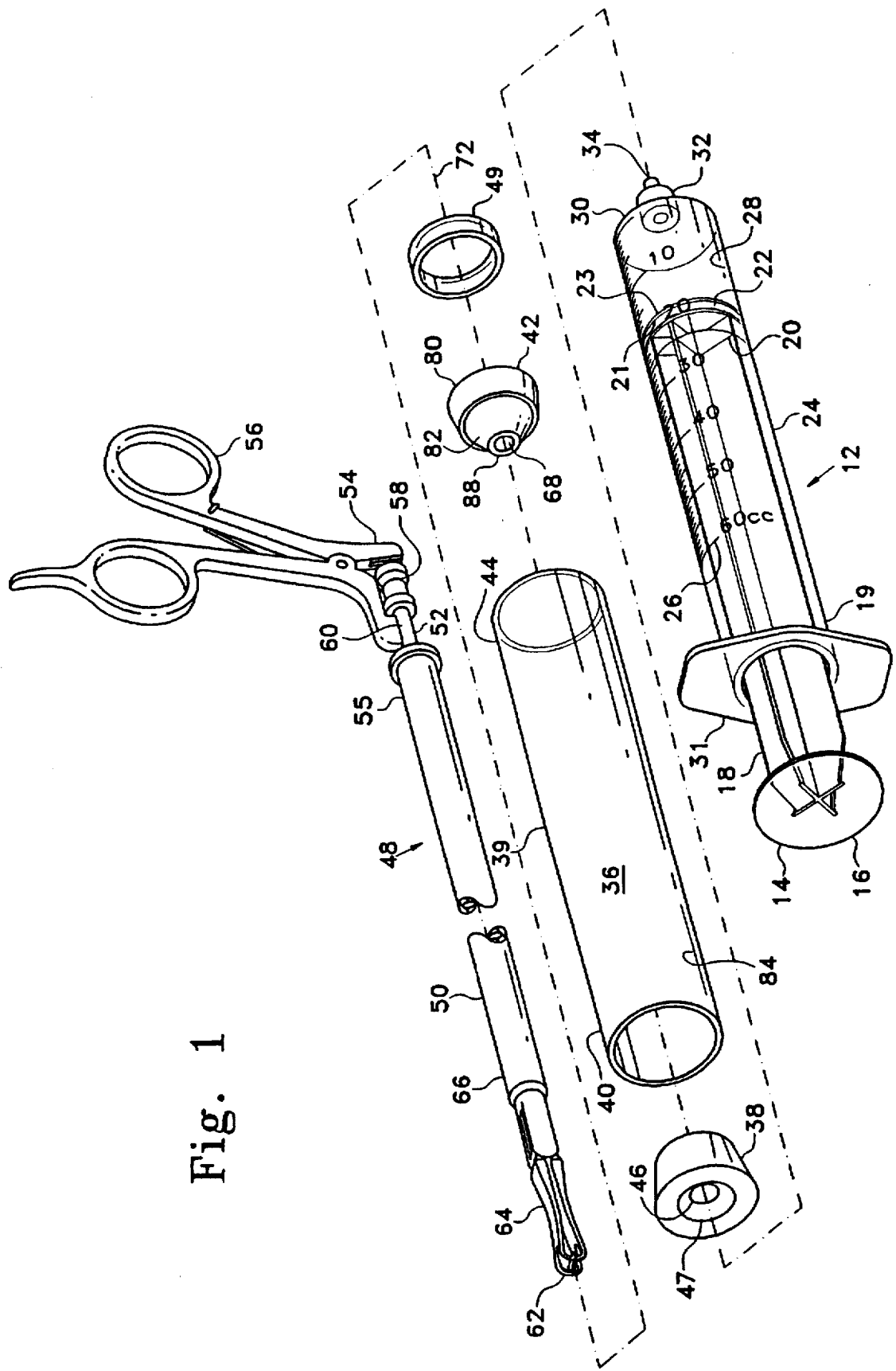
FIG. 1 is an exploded perspective view of one embodiment of an endoscopic cannulated instrument flushing apparatus according to the present invention shown in conjunction with a Babcock tissue grabbing endoscopic instrument for purposes of illustration. The Babcock is shown throughout the drawings as an example of a specific endoscopic instrument being cleaned by the present invention in all embodiments.

Referring now to FIG. 1, there is shown an exploded perspective view of an endoscopic instrument cleaner 10 in conjunction with a Babcock 48 (described below), comprising a syringe 12 having a thumb support 14 integrally formed at a proximal end 16 of a plunger shaft 18 having a distal end 20 fitted with a seal 22. The plunger shaft 18 fits inside a hollow cylindrical body 24, which includes measuring gradation marks 26 and a bifurcated handle portion 31, which allows the body 24 to be placed between the first finger and middle finger with one side of the handle portion 31 resting against the respective two fingers and allowing the user to push the plunger shaft 18 into the body 24 with his thumb. A liquid-tight seal is formed by the seal 22, for example a rubber seal, which bears against the inside wall 28 of the body 24. The plunger shaft 18 is inserted into the body 24 at an open proximal end 19 of the body 24, which accepts the diameter of the circular seal 22, typically an O-ring inserted into a circumferential groove 21 in a head 23 of the plunger shaft 18. The body 24 further includes a distal end 30 having a conical or funnel shape and terminating in a nipple 32. An orifice 34 in the distal end 30 of the body 24 allows fluid communication from the interior of the syringe 12 to an area outside the syringe body 24. The syringe 12 is a conventional disposable syringe, except that in the present invention, no needle is used. In the operation of a conventional syringe, the nipple 32 is immersed into a desired cleaning solution 25 with the plunger shaft 18 pushed into the distal end 30 of the body 24 and then the plunger shaft 18 is drawn away from the distal end 30 (in the direction of the arrows 27 of FIG. 11A) until the desired amount of liquid is drawn into the body 24, as shown in FIG. 11A. Then, when it is desired to expel the liquid from the body 24, the plunger shaft 18 is thrust forward, that is, toward the distal end 30 of the body 24 in the direction of the arrows 29 (FIG. 11B), thereby forcing the cleaning solution 25 in the body 24 through the orifice 34, and therefore through a flush chamber 36. The flush chamber 36 has a body 41 that is preferably cylindrical and is transparent to allow a quick and simple visual confirmation by the worker that the housing 50 of the Babcock 48 is inside the flush chamber 36, allowing the cleaning or flushing solution 25 to enter and exit from the Babcock 48. Because the cleaning solution 25 cannot escape from the apparatus 10, it is forced through the Babcock 48, or other endoscopic instrument, as shown in FIG. 11B. It is important to provide a source of pressurized flowing cleaning, or flushing solution to the flush chamber 36, regardless of the source of that pressurized flowing cleaning solution, for example, a syringe, a manually operated pump, electrical pump, or the like.

Still referring to FIG. 1, a flush chamber 36 comprises a transparent acrylic tube or body 41 having a syringe receiving stopper 38 in a proximal end 40 and an endoscopic instrument receiving stopper 42 in a distal end 44 of the flush chamber 36. The nipple 32 of the syringe 12 is inserted into an aperture 46 in syringe receiving stopper 38, where it is held tight by frictional engagement. An instrument receiving stopper 42 is tightly inserted into the distal end 44 of the flush chamber 36. It has been found that in certain applications, the stopper 42 may be blown out of the flush chamber 36 and it may not be possible to prevent this with conventional adhesives because the flush chamber 36 swells under pressure. This difficulty is easily overcome by inserting the instrument receiving stopper 42 into the flush chamber 36 to create a recess of ¼–⅜ inches (0.635–1.00 cm) at the distal end 44 of the flush chamber 36 and inserting into that recess a tight-fitting sleeve 49 made of the same material as the flush chamber body and binding these two pieces with an organic adhesive that welds the two pieces together. Further, a dye may be added to the adhesive prior to bonding the two pieces together so that the worker can easily see the degree of spreading of the adhesive, with complete coverage of the contact area between the two pieces being desired. In this case frictional engagement as described between the stopper 42, the Babcock 48 and the flush chamber 36 and the reenforcing sleeve insert 49 is sufficient to retain the pieces in their proper spatial relationships without leaks or stopper blowout at up to 110 pounds per square inch ($7.58 \times 10^6$ dynes/cm$^2$) of pressure. This pressure is far greater than the pressure that can be generated by a hand-operated syringe 12 and is far greater than is required to flush gross debris from an endoscopic instrument.

Figure 13:
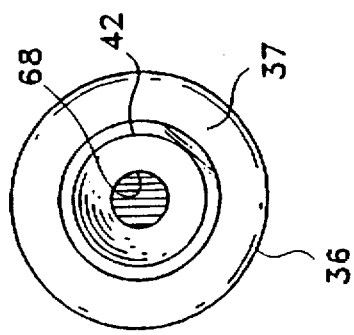
FIG. 13 is a simplified right end elevation of the device of FIG. 2, shown without an instrument inserted therein.
Figure 12:
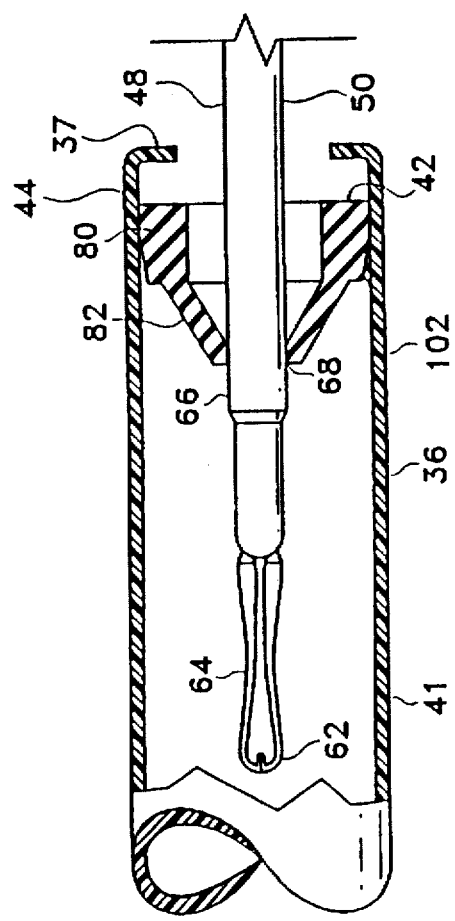
FIG. 12 is an enlarged fragmentary view, partially in cross section, of the instrument receiving end of an alternative embodiment of an endoscopic cannulated instrument flushing apparatus according to the present invention.
Figure 14:
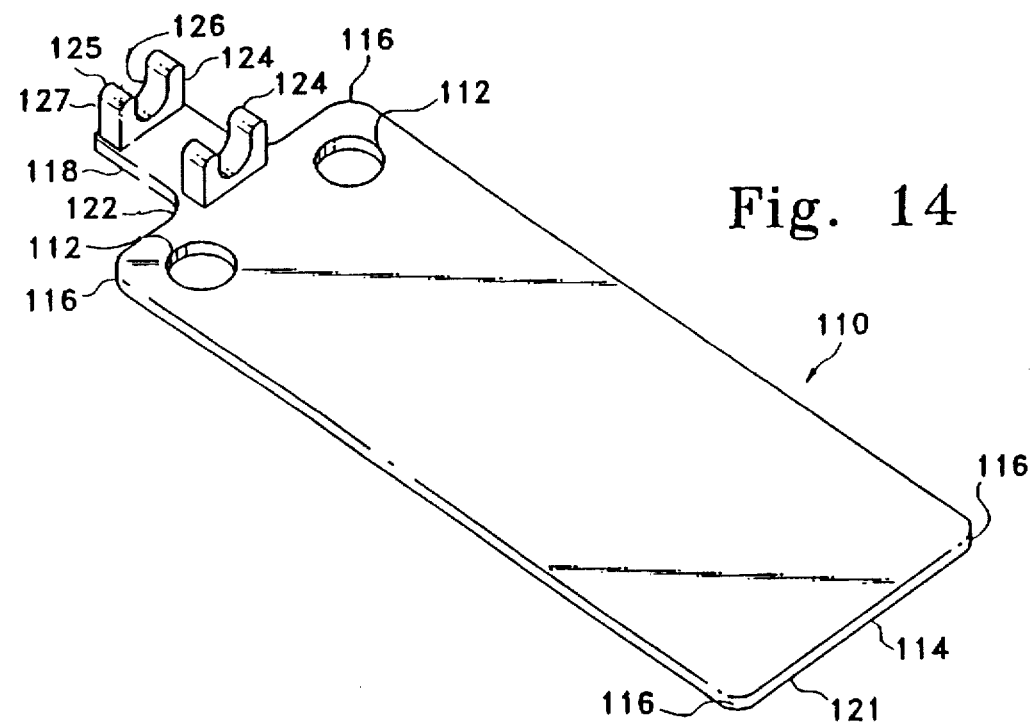
FIG. 14 is a perspective view of an endoscopic cannulated instrument flushing apparatus comprising a flushing board according to the present invention for holding an endoscopic cannulated instrument flushing apparatus and instrument during flushing.
Figure 15:
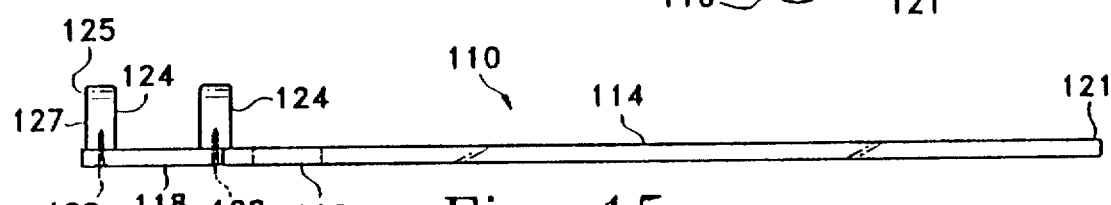
FIG. 15 is a front elevation of the apparatus of FIG. 14.
Figure 16:
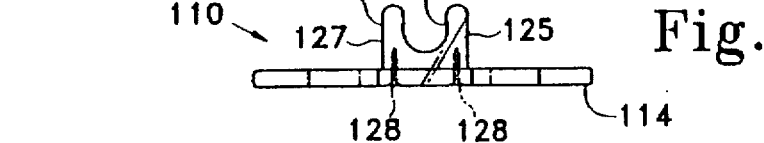
FIG. 16 is a left-side (as shown in FIG. 14) elevation of the apparatus of FIG. 14.
Figure 17:
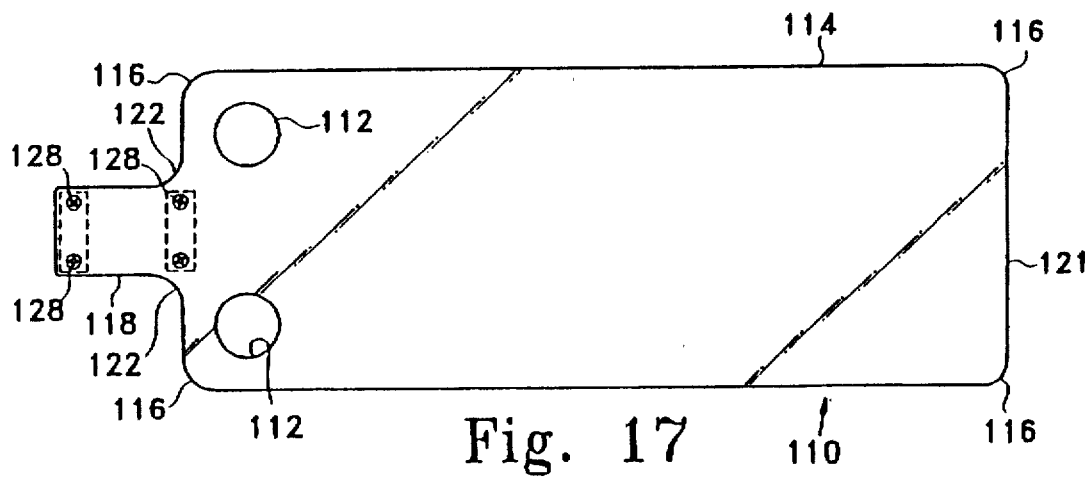
FIG. 17 is a bottom elevation of the apparatus of FIG. 14.

Referring now to FIG. 12, there is shown an alternative embodiment of the flush chamber 36 that utilizes a different structure to address the potential problem of the stopper 42 out of the end of the flush chamber 36. In this alternative embodiment, the distal end 44 of the flush chamber 36 is bent inward uniformly about the circumference or perimeter of the flush chamber 36 to form an inwardly projecting circumferential lip 37 that prevents removal of the stopper 42 through the distal end 44. In the best mode currently known to the inventors for carrying out this formation, the stopper 42 is inserted into the distal end 44 of the flush chamber 36 as shown in the figures. Then the distal end 44 is immersed briefly in hot water, making the flush chamber plastic. The distal end 44 is then pressed downwardly onto a mold having a suitable conical frustum shape, which forms the lip 37. The structure of the lip 37 to prevent blowout of the stopper 42 can naturally be used either with the flush chamber 36 or the flush chamber 102, which is an extension of a syringe hollow cylindrical body 24 (FIG. 7) and the technique for forming the lip 37 may be the same in either case. FIG. 13 provides an end plan view taken from the right-hand side of FIG. 12 and showing the flush chamber without an instrument 48 inserted. FIGS. 12 and 13 make it clear that the lip 37 does not cover the opening of the stopper 42, and therefore does not obscure access to the aperture 68 for receiving the Babcock 48 or other instrument to be flushed.

Figure 10:
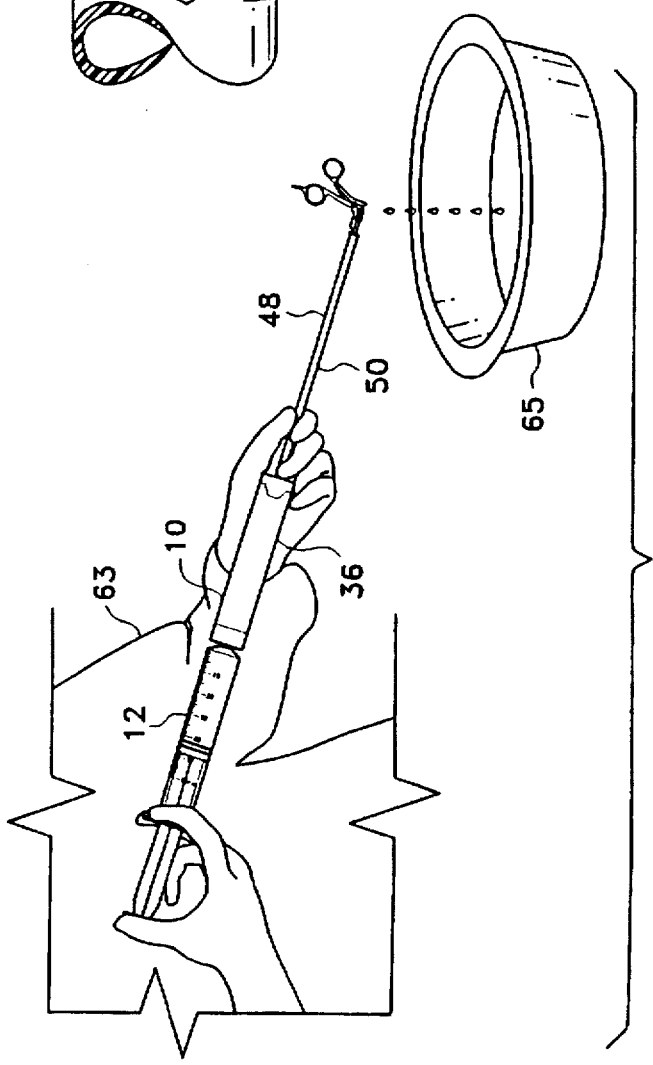
FIG. 10 is an environmental perspective view of the endoscopic cannulated instrument flushing apparatus of FIG. 1 shown in use by a medical worker to clean an endoscopic cannulated instrument, wherein the operation of both embodiments (i.e., of FIGS. 1, 7) is the same.

Referring again to FIG. 1, a Babcock 48 includes an external tubular housing 50, through which instrument control rods 52 are routed. The Babcock 48 includes a proximal end 54 having scissors-like handles 56, which are maintained in a normally closed position by a compression spring 58 mounted about a shaft 60, and a distal end 62 which includes a pair of jaws 64. A Babcock is used for gripping and retracting tissues within the patient's body while working with a minimal incision through which the Babcock 48 is inserted. The distal end 62 of the Babcock 48 is inserted through an aperture 68 in the instrument receiving stopper 42 by a medical worker (FIG. 10). The distal end of the Babcock 48 is inserted into the flush chamber 36 to a depth of about 4–6 inches (10–15 cm), which is sufficient to insure that the distal end 66 of the housing of the Babcock 48 is inside the flush chamber 36. Prior to inserting the Babcock 48 into the flush chamber 36, the syringe 12 and the flush chamber 36 are filled with an appropriate cleaning solution by connecting the syringe 12 to the flush chamber 36, with the plunger shaft 18 of the syringe 12 toward the distal end 30 of the syringe 12, immersing the distal end 44 of the flush chamber 36 into an appropriate cleaning solution, which is then drawn into the endoscopic instrument cleaner 10 by drawing the plunger shaft 18 of the syringe 12 away from the distal end 30 of the syringe. Then the Babcock 48, or other endoscopic instrument, is inserted into and through an aperture 68 in the instrument receiving stopper 42 of the cleaner 10, and the plunger shaft 18 of the syringe 12 is thrust toward the distal end 30 of the syringe 12, forcing the cleaning solution through the tubular housing 50 of the Babcock 48. The cleaning solution is thereby forced through the tubular housing 50 and is expelled at the proximal end 55 of the housing 50 of the Babcock 48, into a suitable drainage basin 65 or the like, as shown in FIG. 10. A Babcock 38 is used here merely to illustrate the use of the endoscopic instrument cleaner 10, which can be conveniently used with any style of endoscopic instrument, including, for example, endoscopes, instruments with rigid external housings, instruments with flexible exterior housings, and so forth.

Referring now to FIG. 2, there is shown a side elevation of the endoscopic instrument cleaner 10 with the Babcock 48 in place for cleaning. It is apparent that the jaws 64 cannot be inserted into the apparatus 10 in any fashion that would allow the plunger head 23 to strike any part of the Babcock 48 or other instrument, because the plunger head 23 cannot enter the flush chamber 36. FIGS. 3 and 6 show the same endoscopic instrument cleaner of FIGS. 1, 2, with the addition of a tubular coupling sleeve 70 made of transparent plastic material that is inserted over the proximal end 40 of the flush chamber 36 prior to inserting the syringe 12 into the flush chamber 36. FIG. 6 provides an enlarged fragmentary view partially in section of the sleeve 70 in place on the endoscopic instrument cleaning apparatus 10. The sleeve 70 fits tightly over the external surface of both the syringe 12 and the flush chamber 36 to reenforce the connection between these two pieces. It has been found that the use of the sleeve 70 provides users of the endoscopic instrument cleaner apparatus 10 with increased confidence in the apparatus, keeps the longitudinal axis 72 of both pieces in alignment, and prevents the syringe receiving stopper 38 from disengaging from the flush chamber 36 under pressure.

FIG. 4 provides an enlarged fragmentary cross sectional view of the instrument receiving stopper 42 illustrating that the stopper 42 is a single piece stopper having a substantially cylindrical base 80 flowing into a conical frustum 82 presenting a circular orifice or aperture 68 that penetrates the entire length of the stopper 42, thereby providing a pathway for insertion of the Babcock 48 jaws 64 and housing 50. The conical frustum shape 82 provides a relatively long line of contact between the Babcock 48 and the stopper 42. Further, the stopper 42 is made of a pliable resilient and elastic material, such as medical grade rubber, and the aperture or bore 68 is deliberately designed to be somewhat smaller than the outside diameter of the instrument housing 50. Therefore, when the instrument housing 50 is inserted through the aperture 42, the instrument housing 50 is gripped very tightly, and, simultaneously, the outer diameter of the cylindrical base 80 of the stopper 42 swells due to insertion of the Babcock 48, causing the stopper 42 to bear against the cylindrical side walls 84, further tightening the stopper 42 in the flush chamber 36. Naturally, the stopper is sized to provide a tight fit into the flush chamber 36 in any case. Further, referring to FIG. 11C, when the plunger 18 of the syringe 12 is thrust toward the distal end 20 of the syringe 12, the cleaning solution inside the syringe body 24 applies pressure to the conical frustum 82, causing the end 88 of the stopper 42 to collapse about the Babcock 48, as shown, further tightening the grip of the stopper 42 on the Babcock 48 and causing the cylindrical base of the stopper 42 to swell tighter against the inside walls 84 of the flush chamber 36. In many uses, the frictional engagement of these members as described in this paragraph is sufficient to prevent blowout of the instrument receiving stopper 42, but as a matter of precaution, the use of the sleeve insert 49 as described above is preferred. In any case, blow-out is not a problem with the syringe receiving stopper 38 because it is relatively much longer than the instrument receiving stopper 42, and therefore has a greater surface area in contact with the flush chamber 36 and, therefore, greater frictional engagement with the flush chamber 36. Naturally, it is possible to provide an instrument receiving stopper that has a longer body, and therefore a greater surface area in contact with the flush chamber 36 and greater frictional engagement, which could prevent blow-out.

FIG. 5 provides an enlarged fragmentary side elevation partially in section illustrating the syringe 12 inserted into the syringe receiving stopper 38 of the flush chamber 36. The stopper 38 has a generally conical frustum body 90 throughout the length of its body and the aperture 46 is cylindrical throughout its length. The aperture 46 is smaller in diameter than is the nipple 32 so that inserting the nipple 32 requires substantial force, which swells the body 90 of the stopper 38 against the inside wall 28 of the body 24, sealing the nipple 32 of the syringe 12 into the stopper 38 and seals the stopper 38 into the flush chamber 36 more firmly. Considerable force is required to force the stopper 38 into the flush chamber 36. The stopper 38 is made from a resilient, elastic flexible material, such as medical grade rubber.

Figure 7:
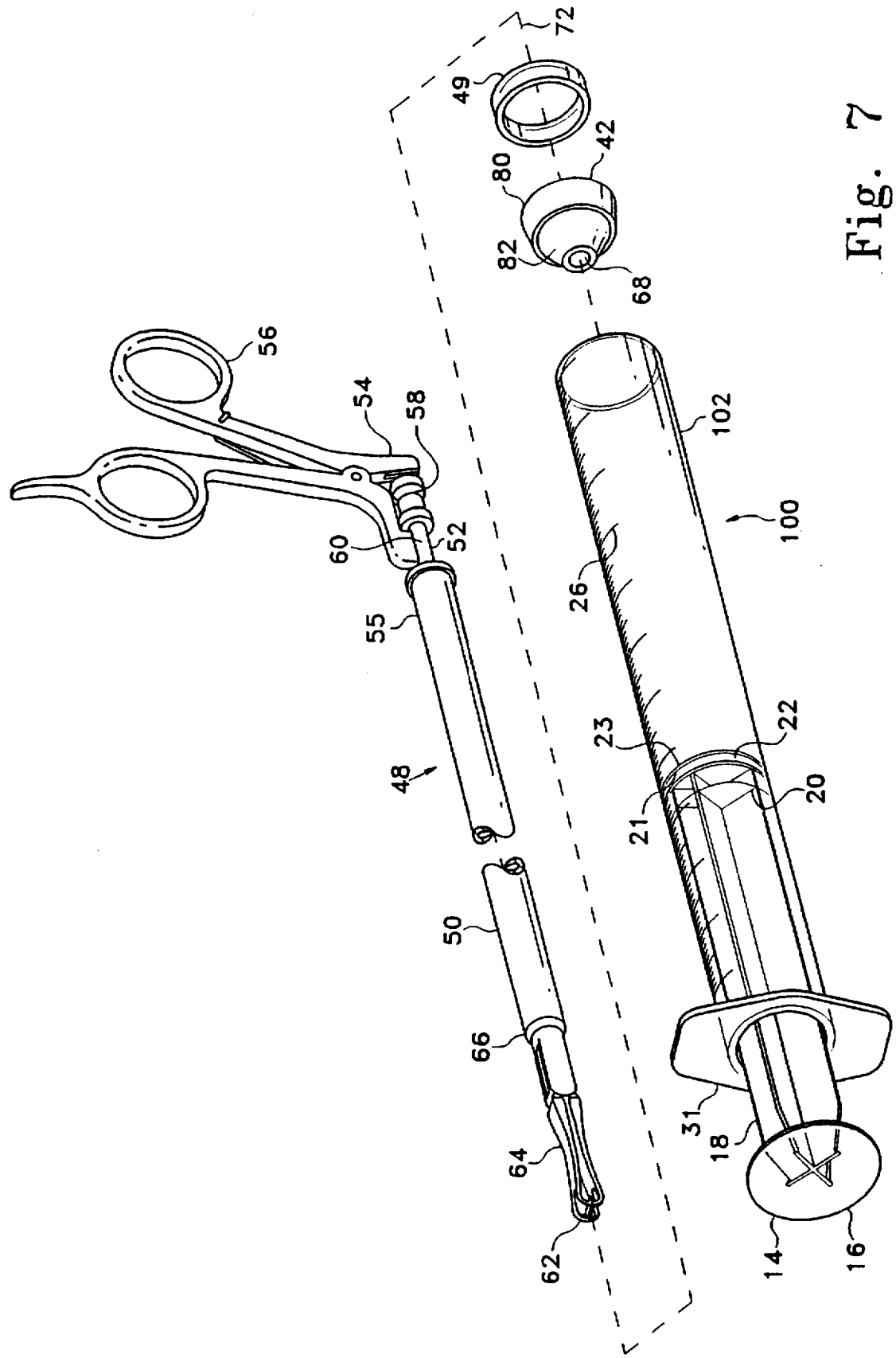
FIG. 7 is an exploded perspective view of an alternative embodiment of an endoscopic cannulated instrument flushing apparatus according to the present invention in which the tubular flushing chamber of the embodiment of FIG. 1 has been built into the body of a syringe.
Figure 8:
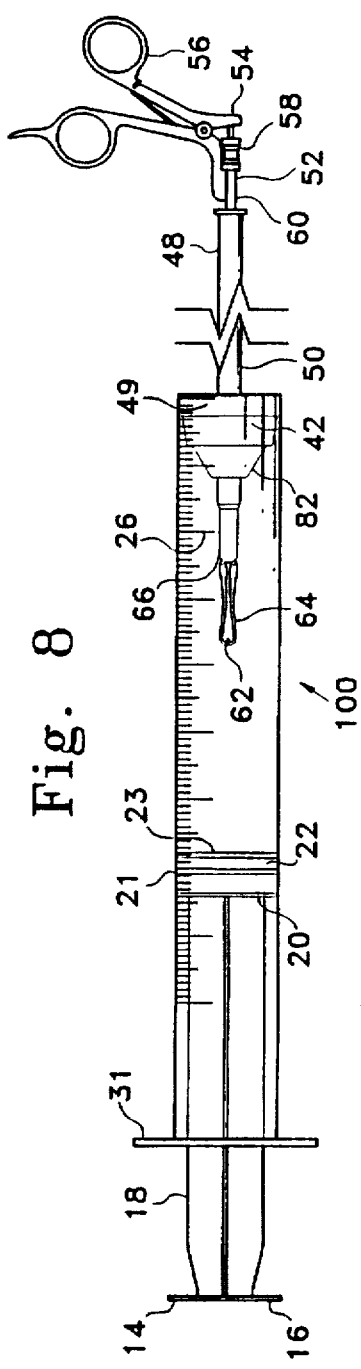
FIG. 8 is a side elevation of the endoscopic cannulated instrument flushing apparatus of FIG. 7.
Figure 9:
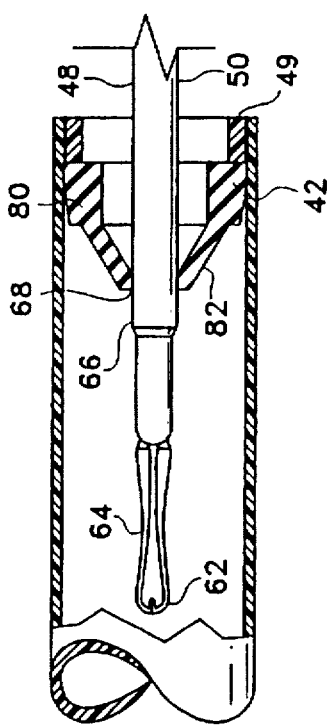
FIG. 9 is an enlarged cross sectional view of a the instrument accepting end of the endoscopic cannulated instrument flushing apparatus of FIGS. 1 and 7.

Referring now to FIG. 7, there is shown an alternative embodiment of an endoscopic instrument cleaning apparatus 100 in which the flush chamber is an extension of the syringe body and, therefore, no syringe receiving stopper is required and no assembly is required prior to use. That is, the flush chamber 36 and the syringe body 24 of FIG. 1 have been combined into a one-piece syringe body and flush chamber 102 in which the flush chamber 102 comprises an elongated body, that is, the flush chamber 102 is longer that the body of a typical syringe relative to the length of the maximum stroke of the plunger shaft 18. The flush chamber 102 and the plunger shaft 18 are of such proportion that the head 23 of the plunger shaft 18 penetrates only a portion of the length of the flush chamber 102 to insure that an endoscopic cannulated instrument can be inserted far enough into the flush chamber 102 for proper cleaning, as described above. The apparatus 100 includes all the conventional syringe 12 components and the instrument receiving stopper 42 and sleeve insert 49 discussed above and so labeled in FIG. 1 and common reference numbers are used for these and other common elements. The apparatus 100 may also include an inwardly projecting circumferential lip 37 about the distal end 44 of the flush chamber 102 (as discussed above and as illustrated in FIGS. 12, 13) as an alternative means to prevent blowout of the stopper 42. Cleaning an endoscopic instrument only requires that the syringe body be filled with cleaning solution and the instrument inserted into the instrument receiving end, and the instrument flushed, as described in greater detail above.

Referring now to FIGS. 14–18 there is shown a flushing board 110 for facilitating use of the endoscopic cannulated surgical cleaning apparatus as discussed to this point. In use it has been found that some workers experience wrist and thumb soreness if they flush many endoscopic cannulated surgical instruments with the present invention in a relatively short period. Further, some difficulty may be experienced in keeping the apparatus and the surgical instrument aligned during flushing. These minor difficulties are overcome by providing additional structure to the invention, namely a flushing board 110. The flushing board 110 includes two grasping holes 112 to make it easier to pick up and carry the flushing board 110. A main body 114 of the flushing board 110 is substantially rectangular with neatly rounded corners 116 in plan view and is relatively thin. The flushing board 110 includes a distal end 121. A neck 118 extends from a proximal end 120 of the flushing board 110 and an opposed pair of neatly rounded corners 122 are located at the juncture of the neck 118 and the main body 114. The neck 118 and the main body 114 are formed from a single sheet of material, which may suitably be a rigid strong plastic material, preferably having a pebble textured nonporous surface for easy cleaning. Alternatively, the flushing board 110 may be made from stainless steel or other material. A pair of yokes 124, each having a central U-shaped channel 126 are fixed to the neck 118 by a plurality of stainless steel screws 128 or other suitable fasteners. The two yokes 124 are spaced apart in parallel relationship along the neck 118 so that their respective U-shaped channels are longitudinally aligned along the neck 118. The centers of the U-shaped channels 126 lie along a longitudinal center line of the flushing board 110. The yokes 124 are made of the same material as the flushing board 110.

Figure 18:
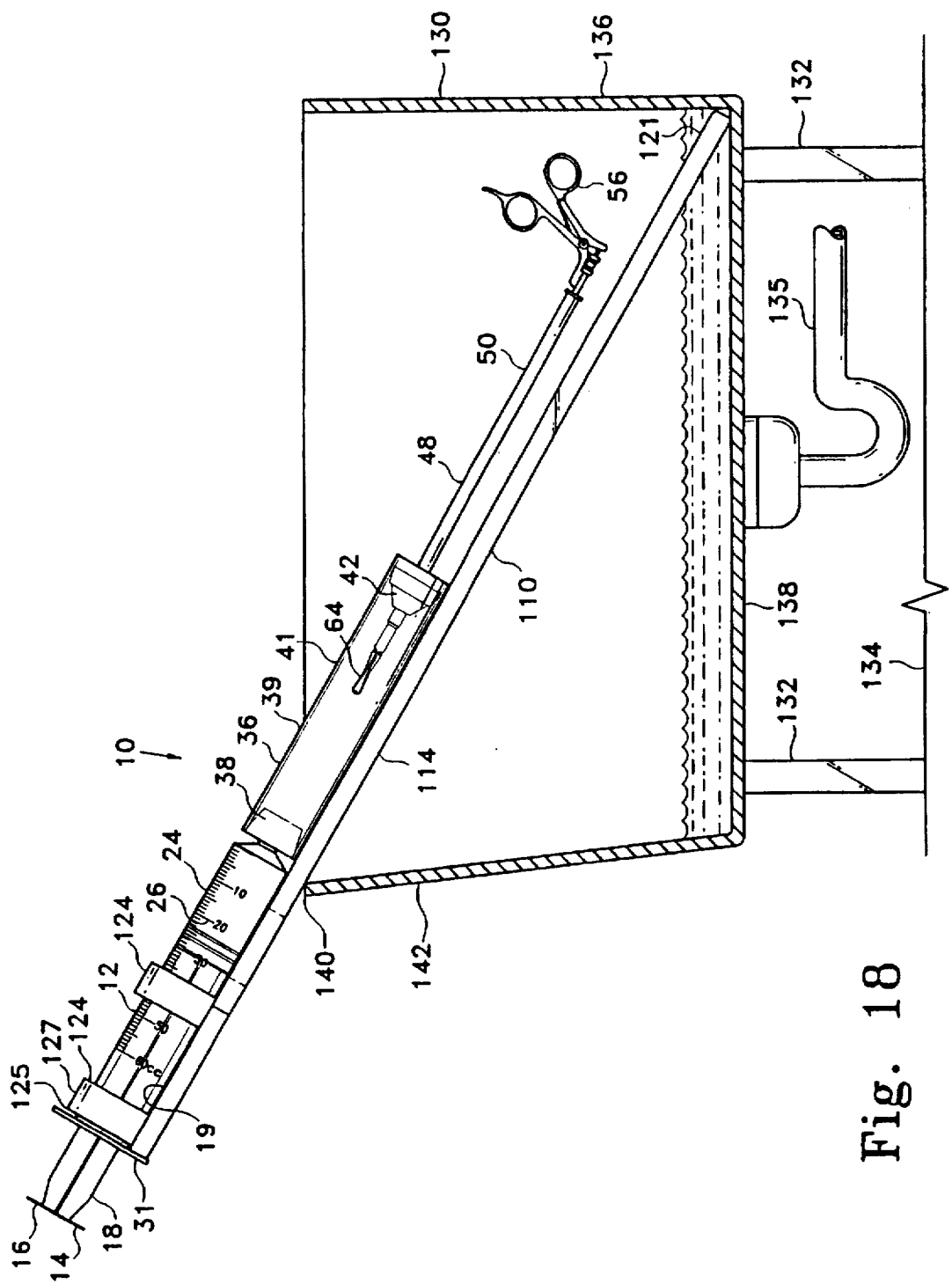
FIG. 18 is a side elevation, partially in cross section, of the endoscopic cannulated cleaning apparatus of the present invention shown in use flushing an instrument in a sink.

Referring now to FIG. 18, there is shown a side elevation, partially in section, of the entire endoscopic cannulated surgical instrument flushing apparatus 10 in use. The flushing board 110 is set into a sink 130 supported by legs 132 standing on a floor 134 and having a suitable drain 135. The distal end 121 is set into the sink 130 against the line joining a side wall 136 and a bottom wall 138 of the sink 130 and the proximal end of the flushing board 110 rests against an upper edge 140 of an opposing side wall 142 of the sink 130. This naturally puts the flushing board 110 on a downward slope with the distal end 121 lower than the proximal end 120 of the flushing board 110.

Still referring to FIG. 18, an apparatus 10 (FIG. 1) or 100 (FIG. 7) is placed on the flushing board 110 with a Babcock 48 inserted for flushing. The syringe body 24 of either embodiment of the apparatus 10, 100 is placed in the two U-shaped channels 126 of the two yokes 124 with the bifurcated handle portion 31 of the syringe body 24 lying against or adjacent to a proximal side 125 of the proximal yoke 127 (see FIGS. 14, 18). The handle portion 31 is wider than the U-shaped channel 126 of either yoke 124, so that the body 24 cannot pass through the yokes 124 when it is placed in the position shown in the drawings and described here.

In use, the worker proceeds as described above, until the actual flushing step. Then the worker places the apparatus 10 or 100, along with the Babcock 48, onto the flushing board as described above. Then the worker merely thrusts the plunger shaft 18 toward the distal end 121 of the flushing board 110 by pressing on the support 14. This can be done with the worker's open palm and allows the worker to utilize the large muscle groups of the arms and chest, reducing strain on the wrist and eliminating strain on the thumb, which need not be used at all. It has been found that this structure enables all workers to flush many endoscopic cannulated surgical instruments without fatigue or soreness. The apparatus comprising the flushing board 110 used in connection with the flushing chamber 102 and the syringe 12 is highly preferred for its simplicity and portability in some settings, such as in the operating room where it is frequently desirable to flush a small number of Babcocks 48 or other instruments during surgeries.

In other settings, however, such as the hospital's principal sterilization facility, it has been further found that workers demand even greater convenience and ease of use because they clean and sterilize very large numbers of instruments. In this case the preferred embodiment illustrated in FIGS. 19–22C is preferable.

Figure 19:
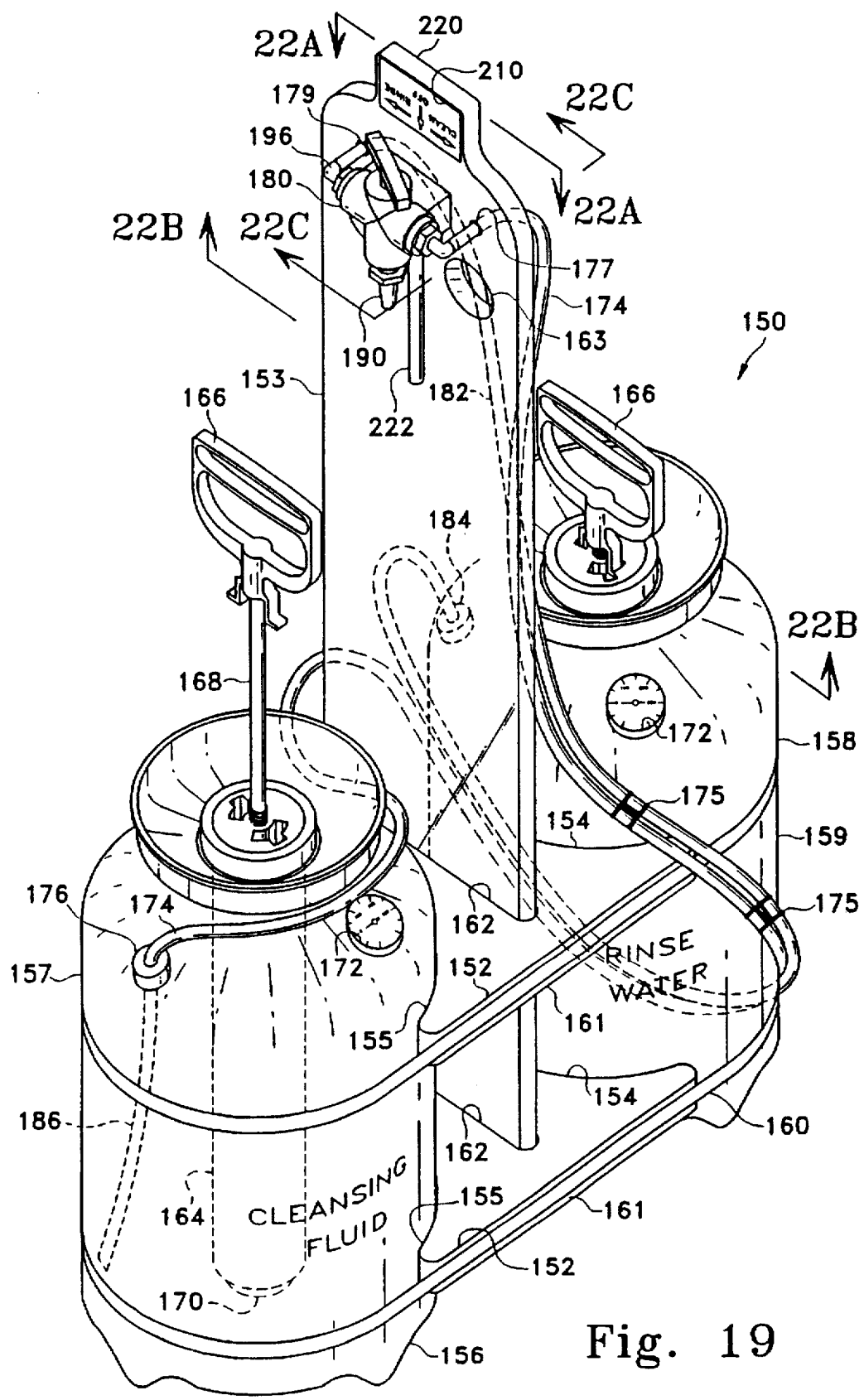
FIG. 19 is a front right perspective view of an automatically pressurized embodiment of the endoscopic cannulated instrument flushing apparatus, showing the flushing board in a stowed position used for storage or transport of the system.

Referring now to FIG. 19, there is shown a right-front perspective view of a self-contained pressurized endoscopic cannulated surgical instrument cleaning apparatus 150 includes a pair of superposed identical frame members 152 having rectangular plan view except for a right-hand concave side 154 and a left-hand concave side 155 (which are identical). A cleaning fluid tank 156 has a basically cylindrical body 157 whose outside diameter fits into the concave sides of the frame members 152. A rinsing water tank 158 has a basically cylindrical body 159 whose outside diameter fits into the concave sides of the frame members 152. In the drawing Figures, the cleaning fluid tank 156 is shown on the left-hand side of the apparatus 150 and the rinsing water tank 158 is shown on the right-hand side of the apparatus 150, but these positions could be reversed without any change in the parts of the apparatus 150. A band 160 is cinched tightly about the upper frame member 152 and the two tanks 156, 158, and another band 160 is cinched tightly about the lower frame member 152 and the two tanks 156, 158, thereby holding the assembly together as a rigid unit. The bands are preferably muffler-type clamps that are tightened with a screwdriver, but any type of band fastener, e.g., nylon webbing with a cinching buckle, could be used. If desired, a groove or channel can be formed along the edge 161 of the frame members 152, but this has proven unnecessary in practice. The frame members 152, 152 are made of polypropolene sheet material, which is easy to work, presents a pleasing finished appearance, is lightweight, durable, resists corrosion and is relatively inexpensive. Each frame member 152 includes a slot 162 for receiving a flushing board 153 for storage whenever the apparatus 150 is not in use. Due to the construction described above, the upper and lower slots 162, 162 are located directly above and below each other, so the flushing board 153 fits into both slots 162, 162 and is held in a vertical position. The flushing board 153 cannot fall out or become dislodged inadvertently unless the apparatus 150 is virtually upside down. To remove the flushing board 153 from the slots 162, 162 the user merely picks it up, optionally using the either or both of the two hand-holes 163.

Each tank 156, 158 includes a hand-operated air compressor 164, which is sealed mostly inside the tank 156 or 158 by threaded screw fittings (not shown) that provide an air-tight seal. A handle 166 fixed to a plunger shaft 168 is attached to a pump inside the air compressor 164 and delivers compressed air to the inside of the tanks 156, 158 through a one-way valve 170 in the bottom of the compressor 164 when the handle 166 is pushed downward. The tanks 156, 158 and the associated compressors 164, 164 are conventional small compressors like those commonly used for small spraying jobs on lawns and gardens. Also included, however, is an air pressure gauge 172 in each tank 156, 158, which are preferably dial indicators. In use, it is desirable to maintain a pressure of about 20 psi ($1.37 \times 10^6$ dynes/cm$^2$) in each of the tanks 156, 158. The tanks 156, 158 can withstand pressures of about 120 psi ($8.27 \times 10^6$ dynes/cm$^2$), but it is extremely difficult to develop a pressure greater than about 40 psi ($2.76 \times 10^6$ dynes/cm$^2$) by using the hand-operated compressors 164, but the desired pressure range of about 15-30 psi ($1.03-2.07 \times 10^6$ dynes/cm$^2$) is relatively easy to obtain and maintain and can easily be done by most health care workers.

One end of a cleaning fluid hose 174 is fixed to a fitting 176 in the cleansing fluid tank 156 and the other end of the hose is connected to a two-line input valve 180 (discussed in detail below) mounted on the flushing board 153. One end of a rinsing water hose 182 is fixed to a fitting 184 in the rinsing water tank 158 and the other end of the rinsing water hose 182 is connected to another inlet line on the two-line input valve 180. Both hoses 174, 182 provide fluid communication with the bottom interior of the respective tanks by means of a straw 186 also connected to each fitting 176, 184. Each straw 186 extends to the bottom of the respective tank so that liquid in each tank can be substantially emptied by positive air pressure inside each tank. The hoses 174, 182 are bound together for convenient handling by a number of cable ties 175. The hoses 174, 182 are routed through apertures 177, 179 respectively in the flushing board 153 so that they are under the flushing board 153 when it is in use. This keeps the hoses 174, 182 out of the way of the user.

An outlet nozzle 190 is connected to the two-line input valve 180 and the proximal end 40 of the flushing chamber 36 is pushed on the outlet nozzle 190, providing a sealing frictional engagement with the receiving stopper 38.

Figure 20:
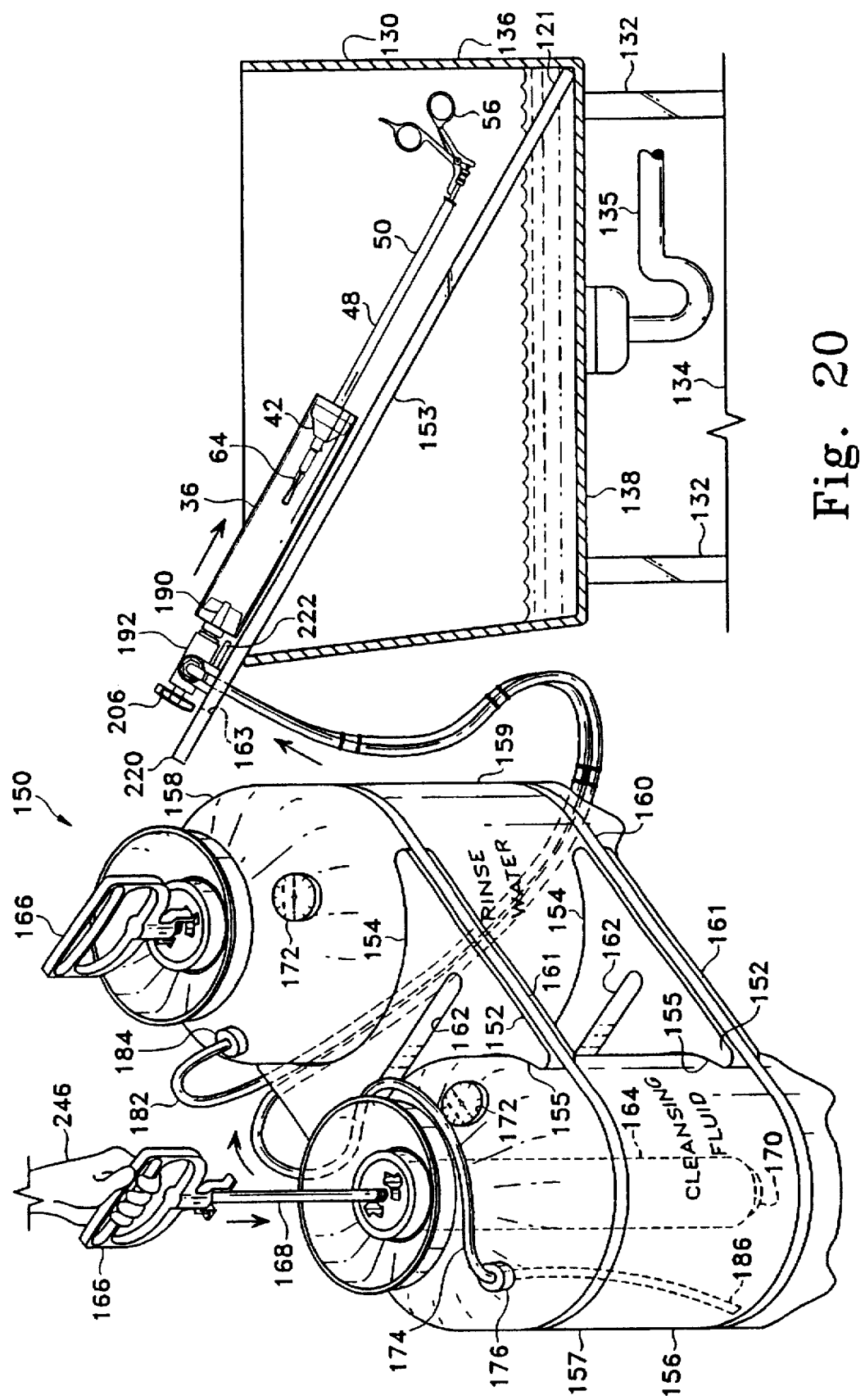
FIG. 20 is a combined view of the apparatus of FIG. 19, showing the operation of the tank and base assembly in right-front perspective and the connected flushing board in use for cleaning an endoscopic cannulated surgical instrument in side elevation and resting in a sink shown in side elevation partially in section.

Referring now to FIG. 20, in use, the flushing board 153 is removed from the storage slots 162 and placed at an angle into a sink 130 as described above. The two-line input valve 180 is fixed to a valve mounting block 240 by a suitable adhesive, and the valve mounting block 240, in turn, is fixed to an upper end 220 of the flushing board 153 by an adhesive (See, e.g. FIGS. 19, 20, 22A–22C, with the best view being FIG. 22C). The valve mounting block 240 thereby serves as a spacer between the valve 180 and the flushing board 153, which allows the valve handle 206 to be rotated through the various positions without interference with the flushing board 153 and allows the flushing chamber 36 and Babcock 48 to lie on the upper surface of the flushing board 153 in alignment with the nozzle 190 (See FIG. 20). The valve mounting block 240 also provides internal fluid flow channels via bores 238, 242 for a pressure release line 222, described below in detail. During use, the flushing chamber 36 lies along the flushing board 153 and the instrument to be flushed is inserted into the instrument receiving stopper 42, as described in detail above.

Figures 21A, 21B, 21C:
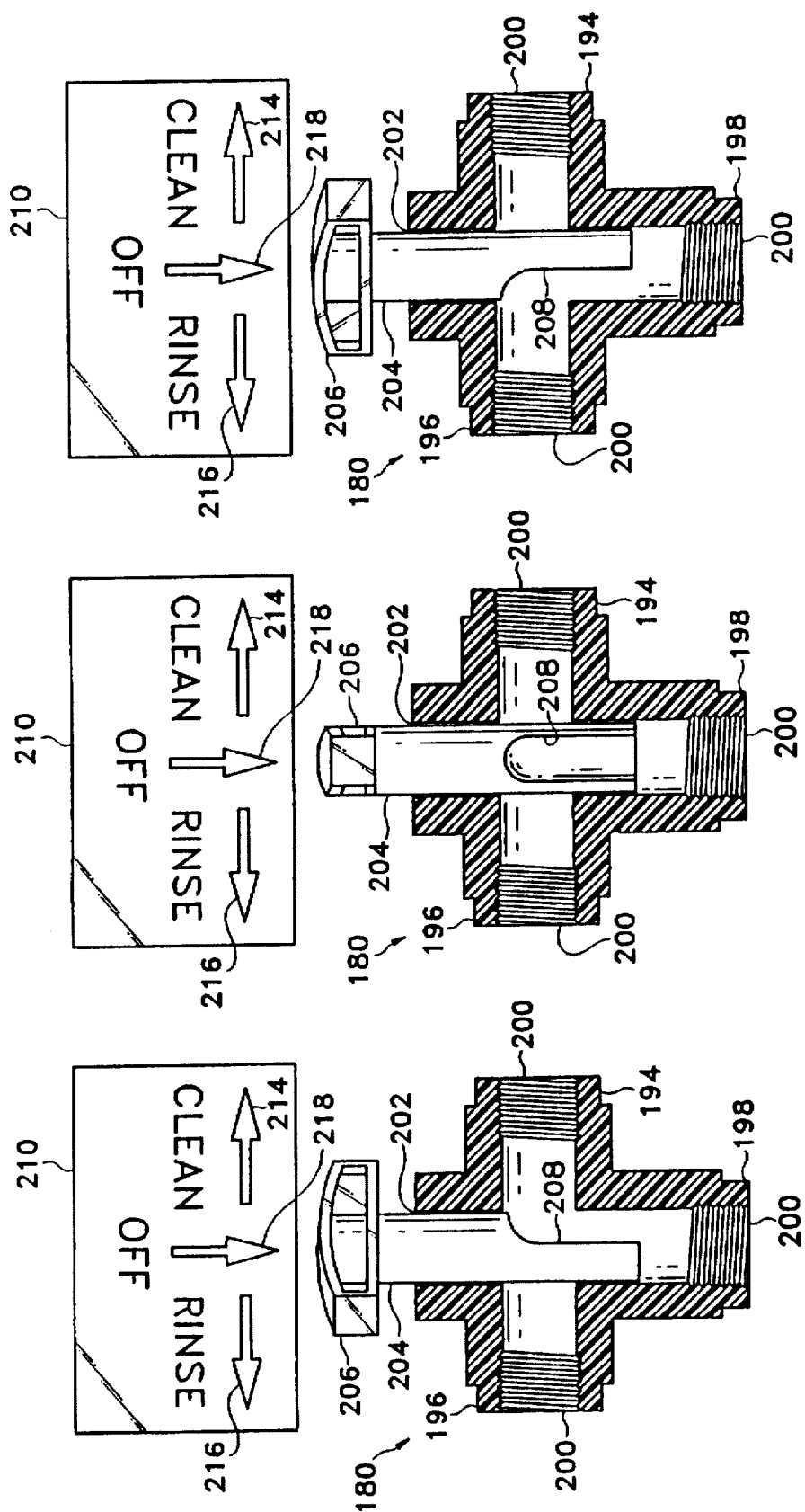
FIG. 21A is a cross section view of the liquid control valve taken horizontally across the valve body, with the valve oriented as shown in FIG. 19, shown with the valve in the "clean" position, i.e., allowing pressurized liquid to flow from the pressurized cleaner tank.
FIG. 21B is a cross section view of the valve of FIG. 21A shown in the "off" position.
FIG. 21C is a cross section view of the valve of FIG. 21A shown in the "rinse" position, i.e., allowing pressurized liquid to flow from the pressurized rinsing tank.

Referring now to FIGS. 21A, 21B and 21C there is shown the valve 180 of FIGS. 19, 20 with the valve body in cross section. The valve 180 includes a valve body 192 having a cleaning fluid inlet channel 194, a rinsing water inlet channel 196 and an outlet channel 198. Each of these three channels includes a bore into the valve body 192 and internal threads 200 at the outer ends of each of the three channels. An access bore 202 receiving a valve stem 204, having an operating handle 206 attached outside the valve body 192 for allowing manual rotation of the valve stem 204 for control of the valve 180. The valve stem 204 includes a scooped out portion 208 in a lower portion 210 of the valve stem 204 for allowing liquid to enter the valve body 192 through either the cleaning fluid inlet channel 194 or the rinsing water inlet channel 196 at one time, but not both at the same time, and then directing the resulting liquid flow through the valve body 192 and out through the outlet channel 196. The direction of flow of liquid through the valve 180 is determined by the direction the scooped our portion 208 is facing. The valve 180 also includes an off position in which neither inlet channel 194, 196 is open. The valve described here is commercially available from a variety of vendors.

An arrow 212 printed on the valve handle 206 (FIG. 22A) indicates whether the valve 180 is closed, open to the cleaning fluid tank 156 or the rinsing water tank 158. The desired position is achieved when the arrow 212 on the valve handle 206 is aligned with a "clean arrow" 214, a "rinse arrow" 216 or an "off arrow" on an instruction label 210 fixed to an upper end 220 of the flushing board 153, as seen in FIGS. 19, 21A, 21B and 21C.

Referring now to FIGS. 22A, 22B and 22C, the external details of the valve 180 and nozzle 190 assembly are shown. A separate elbow fitting 224 is tapped into the internal threads 200 in the cleaning fluid inlet channel 194 and the rinsing water inlet channel 196 via a threaded pipe fitting 226. The hoses 174, 182 are slipped over the ends of the elbow fittings 224 at each respective inlet channel 194, 196 of the valve 180 by a muffler-type hose clamp 228. Each of the hoses 174, 182 is routed through separate apertures 230 through the flushing board 153 so that they do not get in the way of the user during use (e.g., see FIG. 20).

Referring now to FIG. 22C, the outlet nozzle 190 tapers from a threaded fitting 232 that secures the nozzle 190 into the valve outlet channel 198 downward to a tip 234, which includes an outlet orifice 236. The pressure release line 222 is seated and glued in a bore 238 in a valve mounting block 240, and meets a second bore 242 in the mounting block 240 at a right angle. The bore 242 also penetrates into the valve body 192, providing a pressure release channel 239 in the valve body 192 (FIG. 22C). The bores 238, 242 create a channel out of the valve 180 when the valve handle 206 is in the "off" position (i.e., the valve handle 206 is perpendicular to the flushing board 153). When pressurized liquid from either tank 156, 158 fills the flushing chamber 36, some pressure remains in the flushing chamber 36 even after the valve 180 is turned off and this pressure causes liquid to spray uncontrollably from the flush chamber when the Babcock 48 or other endoscopic cannulated surgical instrument is removed from the flushing chamber 36. This undesirable result is eliminated by proving the pressure release line 222 and associated bores 238, 242, which bleeds off pressure from the flushing chamber 36 whenever the valve 180 is in the "off" position, by allowing some small amount of liquid to flow down the flushing board 153.

In use, the cleaning fluid tank 156 is filled to a fill line with a suitable and desired cleaning fluid, such as an enzymatic cleaner and the rinsing water tank 158 is filled to a fill line with rinsing water, which may be tap water or distilled water. Using his hand 246 (FIG. 20), the user operates the pumps 164 to develop the desired pressure in each tank, as discussed above. A flushing chamber 36 is attached to the nozzle 190 via the receiving stopper 38 and the instrument to be flushed is inserted into the flushing chamber 36 via the endoscopic instrument receiving stopper 42. The valve handle 206 two-line input valve 80 is then turned to the cleaning position and the cleaning fluid solution is allowed to flow until it flows from the proximal end 55 of the Babcock 48 or other instrument for 1-2 seconds. Then the valve handle 206 is turned to the rinse position until the rinsing solution flows from the proximal end 55 of the Babcock 48 or other instrument for 1-2 seconds (As the valve handle 206 is moved from the clean position to the rinse position, it passes through the off position, allowing pressure release through the pressure release line 222). Then the valve handle 206 is turned to the off position, allowing removal of the Babcock 48 from the flushing chamber 36 and subsequent insertion of another instrument for cleaning. A large number of instruments can be cleaned on one filling of the tanks 156, 158, with the actual number obviously depending on how much liquid is used for each instrument, but in general, upwards of 100 instruments can normally be expected to be cleaned when the tanks 156, 158 have an effective capacity of about 1 gallon (4 liters) each. During use of 1 gallon (4 liters) of liquid, a tank 156 or 158 will need re-pressurization about 3-5 times. Naturally, it is a simple matter to provide an automatically pressurized system by, for example, providing an electrically operated air compressor to pressurize each tank 156, 158 and to maintain a desired pressure throughout the consumption of all the liquid in a pair of tanks 156, 158. In this case, a pressure release valve is installed in a side wall of the tanks 156, 158 for bleeding off pressure inside the tanks prior to opening them for replenishing the liquids. In general, however, the ease of use, simplicity and affordable cost of the hand-operated unit described in detail here is preferred by hospital workers because it is easily transportable, does not need electricity and hence presents no shock hazard, a great concern when working with electrically conductive liquids that are grounded, and has more than adequate capacity to meet the demand for flushing cannulated endoscopic surgical instruments even in large busy hospitals.

Use of the flushing apparatus 10, 110, 150 supplements the local hospital protocol for cleaning endoscopic cannulated surgical instruments and improves the results of those processes, greatly improving the efficacy of efforts to clean and sterilize such instruments. Independent laboratory tests conducted by a highly regarded testing laboratory in the medical equipment field have been commissioned by the inventors and show great benefits from using the apparatus 10, 110, 150. In scientifically conducted experiments, measured concentrations of spores were introduced into the lumens of cannulated surgical instruments, and it was determined that the conventional practice of soaking the instruments in enzymatic solution or using ultrasonic cleaning techniques neither removes spores from the lumens of these instruments, nor flushes them from the lumens. Thus, conventional cleaning techniques leave spores in place and alive. These spores can easily be introduced into the body cavities of later surgery patients.

Use of the apparatus 10, 110, 150 would be easily justified if it merely removed most gross debris from the instruments, thereby uncovering and exposing spores inside the instruments so that steam or gas could kill them. The independent laboratory tests, however, show that proper use of the apparatus actually removes upwards of 99% of all spores from the instrument, greatly reducing the risk of using endoscopic cannulated surgical instruments.

The independent laboratory tests and experiments were conducted under Good Laboratory Practice Standards, EPA 40, Part 160 and FDA 21 CFR, Part 58. The study was directed by a qualified holder of a Ph.D. and was conducted during the summer of 1993. Original records of the study are recorded at the laboratory. A detailed summary of the independent laboratory tests follows.

Then cannulated instruments were inoculated with about one hundred thousand *Bacillus subtilis* ATCC 19659 spores. The instruments were allowed to dry for 30 minutes at 20 degrees C., plus or minus 1 degree C. Five instruments were exhaustively flushed with sterile deionized water to determine the baseline number of deposited spores. The remaining five instruments were flushed out with 1-20 ml of MetriZyme diluted 1:128, and held at 20 degrees C., plus or minus 1 degree C. for 5 minutes. The MetriZyme was rinsed our with sterile deionized water, and a sample was then taken. Serial 10X dilutions were made, 0.5 ml samples taken and plated on nutrient agar, and plates were incubated at 35 degrees C., plus or minus 2 degrees C. Experimental temperature was 20 degrees, plus or minus 1 degree.

Average before cleaning number of cells in instruments was $2.67\times10^5$ cells/ml, $2.08\times10^5$ cells/ml, and $5.77\times10^5$ cells/ml for the three experiments. Average after cleaning number of cells in the instruments for the three experiments after cleaning by utilizing the flush chamber 36 was $2.40\times10^2$ cells/ml, $1.16\times10^3$ cells/ml, and $9.60\times10^2$ cells/ml. The percent reductions for the experiments were 99.91%, 99.44% and 99.83%. Four out of the 15 after cleaning instruments gave 100% reduction.

To conduct the experiments, *Bacillus subtilis* ATCC 19659 was grown undisturbed in 100 ml soil extract nutrient broth for five days at 35 degrees C., plus or minus 2 degrees C. The culture was then homogenized in a 40 ml tissue grinder and frozen at 0 degrees C. in 2 ml aliquots. A frozen aliquot was thawed, spread onto a nutrient agar plate, and incubated at 35 degrees C., plus or minus 2 degrees C. for 3 days. The culture was observed by staining a heat-fixed, dried slide with Malachite green (7.5% aqueous solution) for 12 minutes and counterstaining with safranin for 30 seconds. About 30% spores were observed. The plate was scraped clean with a rubber policeman and added to 150 ml nutrient broth. The culture was assayed by making serial 10X dilutions in nutrient broth and plating 0.5 ml samples onto nutrient agar.

Ten cannulated instruments were neutralized internally by flushing them with sterile deionized water and then with air.

Using a fresh flushing chamber 36 and syringe 12, the ten cannulated instruments were filled with *B. subtilis* spores and placed sterile autoclave bags to dry for 30 minutes at 20 degrees C., plus or minus 1 degree C.

Using another fresh flushing chamber 36 and syringe 12, sterile deionized water was exhaustively flushed (10-20 ml) through five of the instruments and caught in a sterile 600 ml beaker. The amount of liquid was measured and made up to 100 ml with sterile deionized water. One ml was removed and added to 9 ml nutrient broth. Serial 10X dilutions were made into nutrient broth and 0.5 ml samples were plated onto nutrient agar. The results determined the baseline number of deposited spores. These are the before samples.

The remaining five instruments were flushed with 10–20 ml of MetriZyme diluted 1:128. MetriZyme 1:128 was held in the five instruments for 5 minutes at 20 degrees C., plus or minus 1 degree C. Ten to twenty ml of sterile deionized water was flushed through the lumens of the instruments and discarded. A sample was then taken by catching 10–20 ml of sterile deionized water flushed through the instrument in a 600 ml beaker. The amount of liquid was measured and made up to 100 ml with sterile deionized water. One ml was removed and added to 9 ml nutrient agar. The results determined the number of spores remaining after a cleaning process. These are the after samples.

All plates were incubated overnight at 35 Degrees C., plus or minus 2 degrees C. Experimental temperature was 20 degrees C., plus or minus 1 degree C.

Instruments were tested in random order, so instrument #1 in experiment #1 is not necessarily the same as instrument #1 in experiment #2.

RESULTS

Average before numbers were $2.67 \times 10^5$ cells/ml, $2.08 \times 10^5$ cells/ml in experiments 1, 2, and 3, respectively. Average after numbers were $2.4 \times 10^2$ cells/ml, $1.16 \times 10^3$ cells/ml, and $9.60 \times 10^2$ cells/ml in experiments 1, 2 and 3 respectively. These before and after averages gave percent reductions of 99.99% in experiment 1; 99.44% in experiment 2; and 99.83% reduction in experiment 3.

There were three 100% reductions in experiment 1 one and one 100% reduction in experiment 3.

Culture assays showed that there were $6.00 \times 10^6$ cell/ml present in experiment 1; $1.78 \times 10^6$ cells/ml present in experiment 2; and $6.26 \times 10^6$ cells/ml present in experiment 2 prior to flushing with the flush chamber 36 and syringe 12.

CONCLUSION

In these studies, the *B. subtilis* spores represented a measurable form of soil. The flushing chamber 36 and syringe 12, comprising the apparatus 10, delivered soiled fluids (spores in nutrient broth), cleaning liquids, and rinsing liquids to the small interior lumens of these cannulated grasping medical forceps. The apparatus 10 could thus obviously facilitate delivery of liquids to the lumens of these instruments.

Furthermore, these studies indicated that "soil" as here measured by spores could be at least 99% removed from the lumens when using the apparatus 10. We found the rubber seals between syringe and the flushing chamber 36, and between the cannulated grasping forceps were tight, with no leaks. The apparatus 10 is a convenient and practical apparatus for flushing liquids through the lumens of grasping forceps and other cannulated surgical instruments.

Other embodiments and forms of the invention may occur to those skilled in the art. For example, it may be possible to mold the flush chamber from a single material, including both the instrument receiving stopper and the syringe receiving stopper, or it may be possible to mold a flush chamber having integral internal collars at each end that can be fitted with grommet-like stoppers that provide suitable seals for the syringe and the endoscopic cannulated surgical instrument to be flushed. In another example, the hand-operated syringe, which provides the force for flushing the endoscopic cannulated surgical instrument, may be replaced by a suitable manual or electrical pump used in conjunction with a plurality of different flushing solutions, with each separate flushing solution having a different purpose. Manual pumps may be operated by a handle or foot treadle. Such an arrangement may be expected to reduce the labor costs associated with cleaning such instruments and would standardize the volume of flushing solution used and the pressure and force used during flushing, which could be expected to lead to more uniform results between different institutions and different operators. Further, it may, for example, be desirable to add a reenforcement sleeve to the instrument receiving end of the flush chamber to hold the endoscopic cannulated instrument in longitudinal alignment with the flush chamber without the necessity of holding the instrument by one hand, which will allow a worker to operate the syringe of the preferred embodiment with two hands, and so on. Therefore, while certain forms of the invention have been illustrated and described, the invention is not limited to those embodiments, except insofar as the limitations are included in the following claims.

We claim:

1. A method of cleaning an endoscopic cannulated surgical instrument having proximal and distal ends, the method comprising the steps of:
   (a) providing
      (i) a flush chamber having a proximal end and a distal end;
      (ii) a coupling connected to said proximal end and adapted for communicating a source of pressurized flushing solution into said flush chamber; and
      iii) flexible, resilient means for sealing said distal end relative to an endoscopic cannulated surgical instrument to be flushed, said flexible, resilient distal end sealing means further comprising an aperture for receiving and retaining an endoscopic cannulated surgical instrument by frictional engagement,
   (b) placing the distal end of the endoscopic cannulated instrument through the aperture of the flexible, resilient means and within the flush chamber; and
   (c) communicating flushing solution into the flush chamber through the coupling so that flushing solution flows within the endoscopic cannulated surgical instrument from its distal end toward its proximal end.

2. A device for cleaning a cannulated surgical instrument having a tubular portion with an outer diameter, the device comprising:
   (a) a flush chamber having a proximal end, inner surfaces defining a diameter, and a distal end, the diameter defined by the inner surfaces of the flush chamber being substantially larger than the outer diameter of the tubular portion of the cannulated surgical instrument;
   (b) a coupling connected to said proximal end and adapted for communicating a source of pressurized flushing solution into said flush chamber; and
   (c) flexible, resilient means for sealing said distal end relative to a cannulated surgical instrument to be flushed, said flexible, resilient distal end sealing means further comprising an aperture for receiving and retaining a cannulated surgical instrument by frictional engagement.

* * * * *